(12) United States Patent  (10) Patent No.: US 8,183,235 B2
Shiina  (45) Date of Patent: May 22, 2012

(54) DIHYDRONAPHTHALENE COMPOUND AND USE THEREOF

(75) Inventor: Isamu Shiina, Tokyo (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 288 days.

(21) Appl. No.: 12/675,331

(22) PCT Filed: Sep. 11, 2008

(86) PCT No.: PCT/JP2008/066384
§ 371 (c)(1),
(2), (4) Date: Feb. 25, 2010

(87) PCT Pub. No.: WO2009/035020
PCT Pub. Date: Mar. 19, 2009

(65) Prior Publication Data
US 2010/0249400 A1    Sep. 30, 2010

(30) Foreign Application Priority Data

Sep. 11, 2007  (JP) .................................. 2007-235933

(51) Int. Cl.
*A61K 31/55* (2006.01)
*C07D 401/02* (2006.01)
(52) U.S. Cl. .................................. 514/217.03; 540/596
(58) Field of Classification Search ........................ None
See application file for complete search history.

(56) References Cited

U.S. PATENT DOCUMENTS 3,274,213 A    9/1966   Lednicer

FOREIGN PATENT DOCUMENTS

| EP | 1336602 | * | 8/2003 |
| JP | 2006-117648 | | 11/2006 |
| JP | 2007-224016 | | 6/2007 |

OTHER PUBLICATIONS

Fred L. Steinbaum et al., "Clinical Trial of Nafoxidine in Advanced Breast Cancer", Medical and Pediatric Oncology, 1978, vol. 4, pp. 123-126.

"Uterine Expression of Vascular Endothelial Growth Factor Is Increased by Estradiol and Tamoxifen," Salman M. Hyder, et al., Cancer Research 56, Sep. 1, 1996, 3954-3960.

* cited by examiner

*Primary Examiner* — Noble Jarrell
(74) *Attorney, Agent, or Firm* — Day Pitney LLP

(57) ABSTRACT

Disclosed is a compound represented by the formula (I) below as a dihydronaphthalene compound having a chemical structure which is excellent in production efficiency when compared with lasofoxifene and nafoxidine. This compound is useful as a proteasome inhibitor and/or an antitumor agent.

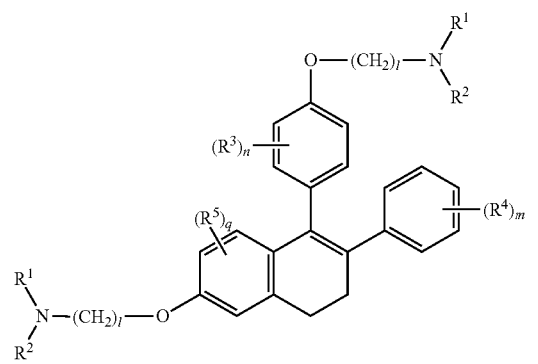

(In the formula, two $—(CH_2)_l—N(R^1)(R^2)$ groups represent a same substituent; $R^1$ and $R^2$ each represents a hydrogen atom, or a same or different alkyl group; or alternatively, $R^1$ and $R^2$ may combine together to form a monocyclic heterocyclic ring with a nitrogen atom having them or additionally together with one or more atoms selected from an oxygen atom, a sulfur atom and a nitrogen atom; $R^3$, $R^4$ and $R^5$ each represents one or more substituents selected from a hydrogen atom, an alkyl group, an acyl group, an alicyclic group, an aromatic group, a halogen atom, an acyloxy group, a cyano group and a nitro group; l represents an integer of 2-5; n represents an integer of 1-4; m represents an integer of 1-5; and q represents an integer of 1-3.)

4 Claims, 1 Drawing Sheet

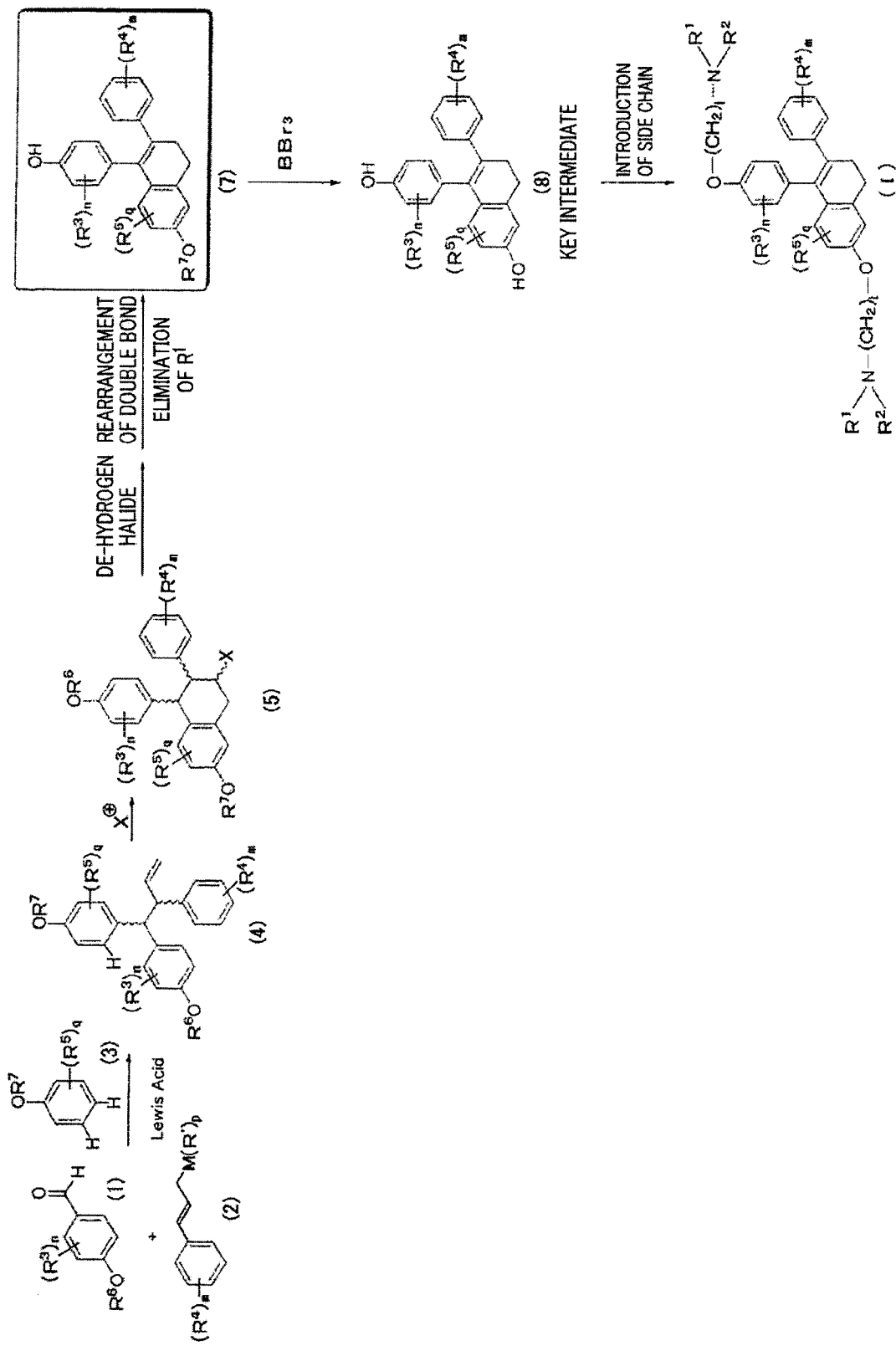

DIHYDRONAPHTHALENE COMPOUND AND USE THEREOF

This application is a 371 of International Application No.: PCT/JP2008/066384, filed Sep. 11, 2008, which in turn claims priority from Japanese Application No.: 2007-235933, filed Sep. 11, 2007. Both applications are incorporated herein by reference.

TECHNICAL FIELD

The present invention relates to a novel dihydronaphthalene compound, and to a proteasome inhibitor and anticancer agent including this compound as an active ingredient.

BACKGROUND ART

Compounds of lasofoxifene, nafoxidine and the like are known as selective estrogen receptor modulators (SERM's). "Selective estrogen receptor modulator" is a generic term for pharmaceuticals which show an estrogen action, or which show an anti-estrogen action, depending on the organ or tissue. For example, such a pharmaceutical may show an anti-estrogen action with respect to the uterus, mammary glands or the like, while on the other hand showing an estrogen action with respect to postmenopausal osteoporosis, serum cholesterol, the cardiovascular system and the like. As such pharmaceuticals, in addition to lasofoxifene and nafoxidine, others such as tamoxifen and raloxifene are also known.

Among these, lasofoxifene shows promise as an agent for the prevention and treatment of postmenopausal osteoporosis, and currently large scale clinical trials are underway. The chemical structure of lasofoxifene, cis-6-phenyl-5-[4-(2-pyrrolidine-1-yl-ethoxyphenyl]-5,6,7,8-tetrahydronaphthalen-2-ol, is shown by the following Formula (30).

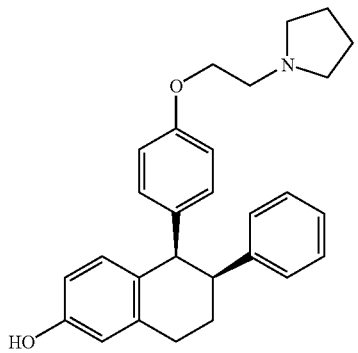

(30)

However, lasofoxifene has a tetrahydronaphthalene skeleton, and has geometric isomers, but because only the cis form has effects, an isolation step is necessary.

Further, the chemical structure of nafoxidine is shown by the following Formula (31).

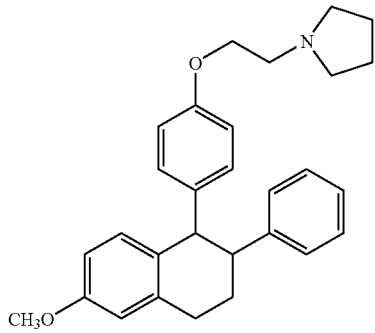

(31)

Nafoxidine has a 1,2-dihydronaphthalene skeleton, and because there are two substituent groups bonded to two double bonded carbons, it has no geometrical isomers, but one of the two hydroxyl groups is substituted by methyl group, and the other is substituted by a 1-pyrrolidinylethyl group, and because a positional isomerism arises, the production efficiency becomes low.

DISCLOSURE OF THE INVENTION

Problems to be Solved by the Invention

The objective of the present invention is to newly synthesize dihydronaphthalene compounds having a chemical structure which is excellent in production efficiency compared to lasofoxifene and nafoxidine, as well as to investigate novel pharmaceutical uses of these novel dihydronaphthalene compounds, and in addition to finding useful new compounds, to provide a novel pharmaceutical having these compounds as their active ingredients.

Means for Solving the Problems

The present inventors, as a result of diligent research, synthesized novel dihydronaphthalene compounds with very high production efficiency, and which does not give rise to geometrical isomerism or positional isomerism in its production process. Further, while investigating novel actions of these dihydronaphthalene compounds, it was discovered that some of these compounds show a proteasome inhibition action which was until present completely unknown as a pharmaceutical effect of an analogue of lasofoxifene or nafoxidine.

There is an ubiquitin-proteasome system which accomplishes an important role as a selective protein breakdown system inside the cell, and it has become clear that this system participates in various biogenic activities such as the cell cycle, transcription, signal transduction, apoptosis, metabolism, antigen presentation and the like. This proteasome has an action of ATP-dependent breakdown of several target proteins linked to ubiquitin, and has three types of active sites for trypsin, chymotripsin, and caspase. In recent years, the development of anticancer agents which kill cancer cells by accumulating abnormal proteins in the cancer cells, by suppression of the functioning of the proteasome of the cancer cells has been carried out, and BORTEZOMIB (Velcade; registered trademark), which is one type of proteasome inhibitor, has been approved as a pharmaceutical for the treatment of intractable multiple myeloma (year 2003).

When ascertaining a like anticancer action for the above dihydronaphthalene compounds, most of these compounds were found to show an anticancer action.

Further, such a proteasome inhibitor is also a prospective treatment agent for not only cancer, but also inflammatory diseases and immune diseases.

Furthermore, the above accumulation of abnormal proteins within the cell has been proposed as a common mechanism for the onset of various neurodegenerative diseases such as Alzheimer's disease, Parkinson's disease, prion disease and the like, and thus a proteasome inhibitor can be useful for clarifying the origin of such neurodegenerative diseases or for development research of therapeutic drugs.

Further, the present inventors, when searching for novel actions of the dihydronaphthalene compounds, learned that among these compounds, there are some which while not showing a clear proteasome inhibition action, do show an anticancer action.

Accordingly, the above dihydronaphthalene compounds synthesized by the present inventors are novel compounds, and moreover, in addition to being very advantageous in terms of synthesis due to their structural features, there are no other existing proteasome inhibitors or anticancer agents with analogous structures, and therefore, the present inventors believe that they may become leading compounds as proteasome inhibitors and anticancer agents, and thus completed the present invention.

Specifically, the present invention is as follows.

The first aspect of the present invention is the compound according to the below formula (I).

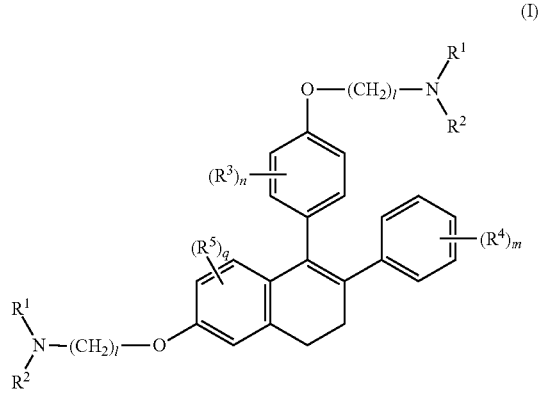

(in the formula, the two

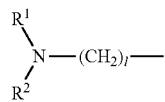

are the same substituent group, $R^1$ and $R^2$ are hydrogen atoms, or respectively the same or different alkyl groups, and $R^1$ and $R^2$ may form a monocyclic heterocycle together with the nitrogen atom to which they are attached, or further together with one or more of an oxygen atom, sulfur atom, and nitrogen atom; $R^3$, $R^4$ and $R^5$ are each one or more substituent group selected from a hydrogen atom, alkyl group, acyl group, alicyclic group, aromatic group, halogen atom, acyloxy group, cyano group, and nitro group, l is an integer of 2 to 5, n is an integer of 1 to 4, m is an integer of 1 to 5, and q is an integer of 1 to 3).

The second aspect of the invention is the compound according to the below formula (II).

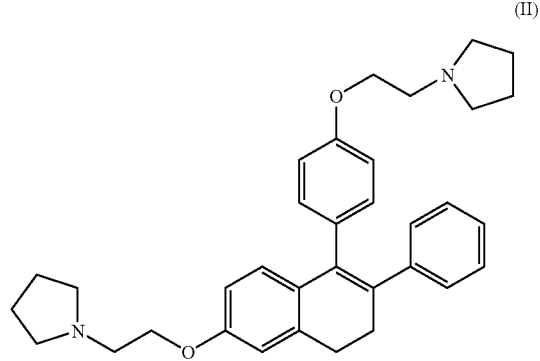

The third aspect of the invention is the compound according to the below formula (III).

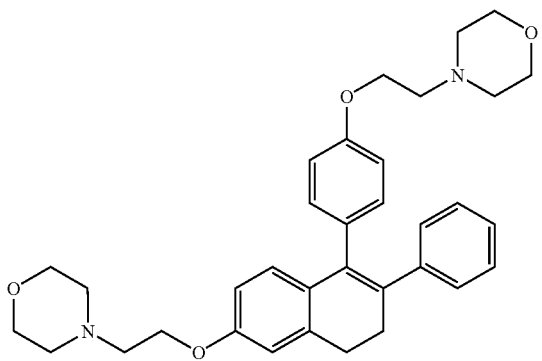

The fourth aspect of the invention is the compound according to the below formula (IV).

(IV)

The fifth aspect of the invention is the compound according to the below formula (V).

(V)

The sixth aspect of the invention is the compound according to the below formula (VI).

(VI)

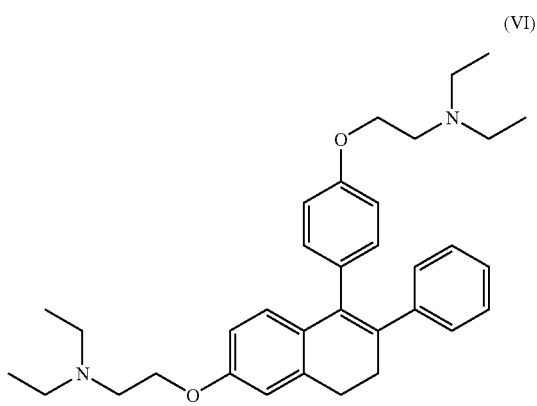

The seventh aspect of the invention is the compound according to the below formula (VII).

(VII)

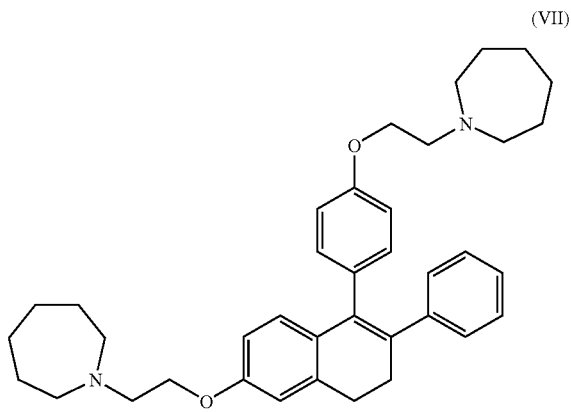

The eighth aspect of the invention is the compound according to the below formula (VIII).

(VIII)

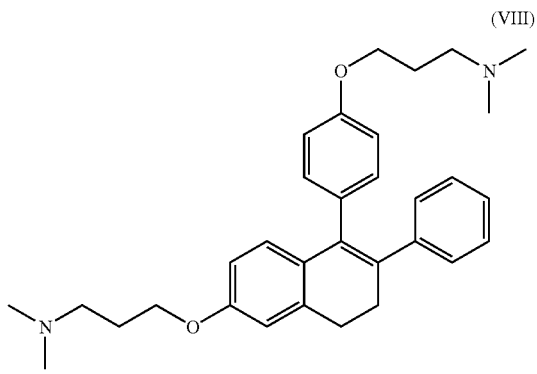

The ninth aspect of the invention is a proteasome inhibitor comprising as an active ingredient the compound according to any one of the above second, third, and fifth to seventh aspects.

The tenth aspect of the invention is an anticancer agent comprising as an active ingredient the compound according to any one of the above second and fourth to eighth aspects.

Effects of The Invention

The novel dihydronaphthalene compound of the present invention shows a proteasome inhibition action and/or an anticancer action. In comparison, there are no reports of the lasofoxifene analogues or nafoxidine analogues of the prior art showing such actions. On the other hand, the lasofoxifene of the prior art has cis and trans isomers as geometric isomers, and of these, because only the cis isomer is effective it is necessary to isolate the cis isomer, whereas because the dihydronaphthalene compound of the present invention does not have isomers, there is no need for an isolation step. Further, nafoxidine, as is clear from the above formula (31), does not have geometric isomers, but because the two hydroxyl groups on the nafoxidine skeleton are respectively substituted with different alkyl groups, positional isomerism arises in its production, and the production efficiency decreases. In contrast, the dihydronaphthalene compound of the present invention has a nafoxidine skeleton, but because the two hydroxyl groups are substituted by the same side chains, this positional isomerism does not arise.

Moreover, many of the means of production of the compounds of the prior art known as proteasome inhibitors and anticancer agents require multiple steps, and because of this there are problems in terms of synthesis. In contrast, the dihydronaphthalene compounds of the present invention have no isomers and are efficient and easy to synthesize, and further, there are no proteasome inhibitors and anticancer agents of the prior art having analogous structures. Accordingly, not only is the dihydronaphthalene compound of the present invention itself useful as a proteasome inhibitor and anticancer agent, but it also has the potential to become a lead compound for the development of novel proteasome inhibitors and anticancer agents. Further, it greatly contributes not only as an anticancer agent, but also for the treatment of inflammatory and immune disorders, and the research and development of various neurodegenerative diseases such as Alzheimer's disease, Parkinson's disease, prion disease and the like.

BRIEF DESCRIPTION OF THE DRAWINGS

FIG. 1 is a schematic diagram showing each step in the production method of the dihydronaphthalene compound of the present invention.

PREFERRED MODE FOR CARRYING OUT THE INVENTION

The dihydronaphthalene compound used as a proteasome inhibitor and/or anticancer agent in the present invention is shown by the following formula (I).

(I)

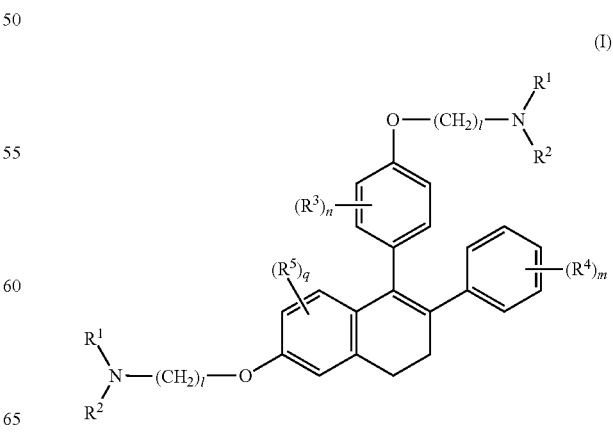

(in the formula, the two

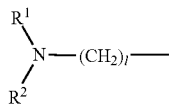

show the same substituent group, $R^1$ and $R^2$ are hydrogen atoms, or are each the same or different alkyl groups, and $R^1$ and $R^2$ may form a monocyclic heterocycle together with the nitrogen atom to which they are attached, or further together with one or more of an oxygen atom, sulfur atom, and nitrogen atom; $R^3$, $R^4$ and $R^5$ are each one or more substituent group selected from a hydrogen atom, alkyl group, acyl group, alicyclic group, aromatic group, halogen atom, acyloxy group, cyano group, and nitro group; l is an integer of 2 to 5, n is an integer of 1 to 4, m is an integer of 1 to 5, and q is an integer of 1 to 3.)

In the compound of the above formula (I), as the monocyclic heterocyclic group formed by $R^1$ and $R^2$, a 5 to 7 membered ring is desirable, for example a pyrrolidinyl group, a piperidinyl group, a piperazinyl group, a morpholinyl group, a thiomorpholinyl group, and a diaza-cyclohexyl group can be mentioned.

As the characteristics of this chemical structure, there are the points that it has no 1,2,3,4-tetrahydronaphthalene ring as in lasofoxifene, but has a 1,2-dihydronaphthalene ring, and the carbon atoms of the double bonds at the 1,2 positions are both substituted with phenyl groups, so that there are no geometrical isomers as in lasofoxifene, and that further, the 7 position of the 1,2-dihydronaphthalene ring as well as the phenyl group of the 1 position are substituted by identical side chains.

Further, as representative examples of the proteasome inhibitors known in the prior art, Bortezomib, Lactacystin, Mg132 and the like can be mentioned, but these are oligopeptide type compounds and have isomers.

In contrast, the dihydronaphthalene compound of the present invention shown in the formula (I) has a completely different structure from an oligopeptide and in addition, it can be produced without having a means for isolating isomers in the production method. As specific compounds shown by the formula (I) of the present invention, for example the following can be mentioned.

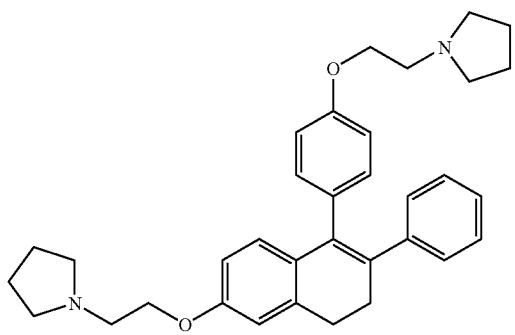

(II)

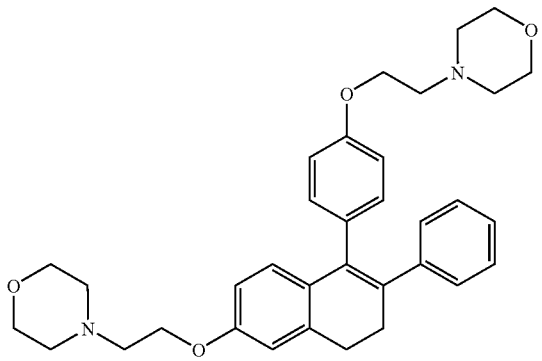

(III)

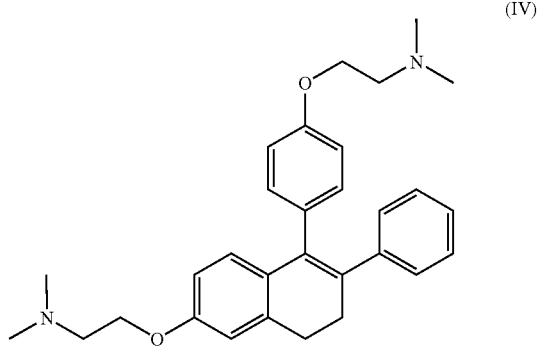

(IV)

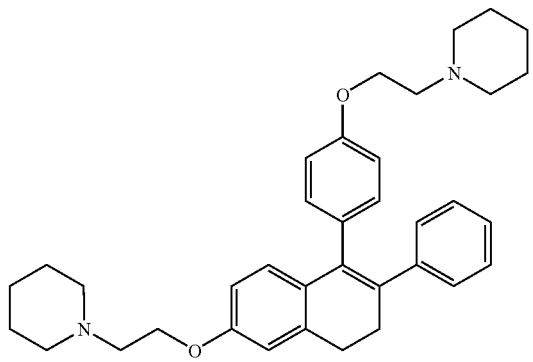

(V)

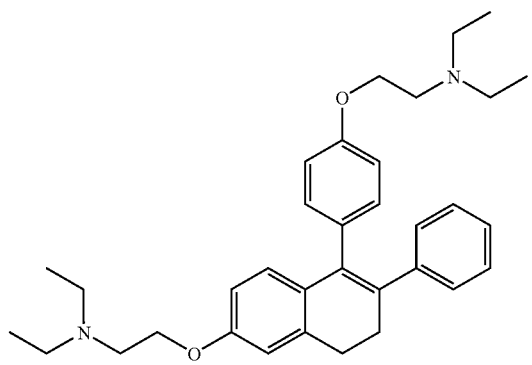

(VI)

-continued

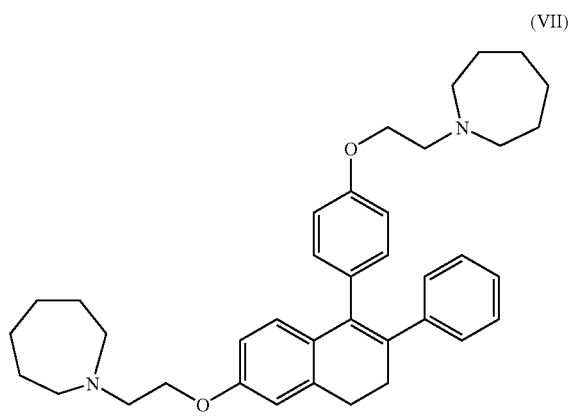
(VII)

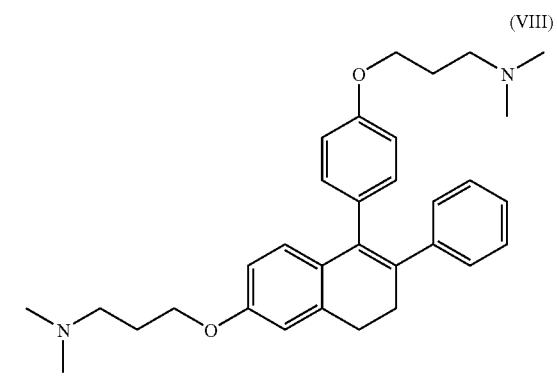
(VIII)

These compounds (I) to (VIII) of the present invention are all novel compounds which have not been disclosed in the literature.

Below, the production method of the dihydronaphthalene compounds shown in formula (I) are explained with reference to FIG. 1.

Method of Production (FIG. 1)

Step 1 (Step of Coupling 3 Components)

In the present invention, first, the compound of formula (1), the compound of formula (2), and the compound of formula (3) below are used as raw material compounds and in one step, the compound of formula (4) is synthesized.

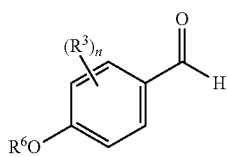
(1)

(in the formula, $R^6$ is a hydrogen atom, alkyl group, acyl group, alicyclic group, or aromatic group, $R^3$ is one or more substituent group selected from a hydrogen atom, alkyl group, acyl group, alicyclic group, aromatic group, halogen atom, hydroxyl group, alkyloxy group, acyloxy group, cyano group, and nitro group, and n is an integer of 1 to 4).

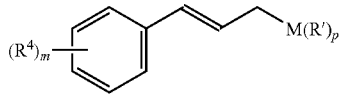
(2)

(in the formula, R' is one or more substituent group selected from a hydrogen atom, alkyl group, acyl group, alicyclic group, aromatic group, halogen atom, hydroxyl group, alkyloxy group, acyloxy group, and cyano group, M is a silicon atom, boron atom, tin atom, zinc atom, or magnesium atom, $R^4$ is one or more substituent group selected from a hydrogen atom, alkyl group, acyl group, alicyclic group, aromatic group, halogen atom, hydroxy group, alkyloxy group, acyloxy group, cyano group and nitro group, m is an integer of 1 to 5, and p is an integer of 1 to 4).

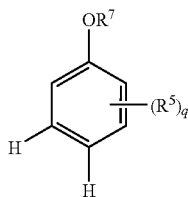
(3)

(in the formula, $R^7$ is a hydrogen atom, alkyl group, acyl group, alicyclic group, or aromatic group, $R^5$ is one or more substituent group selected from a hydrogen atom, alkyl group, acyl group, alicyclic group, aromatic group, halogen atom, hydroxyl group, alkyloxy group and acyloxy group, and q is an integer of 1 to 3).

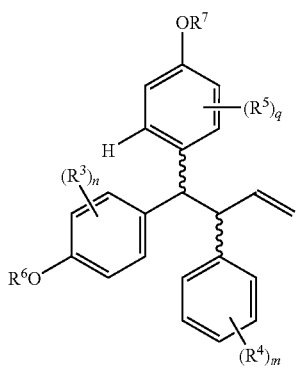
(4)

(in the formula, $R^3$ to $R^7$, and n, m and q are respectively as above, and the wavy line indicates an R or S configuration bond).

As preferable compounds of those shown in formula (1), for example 4-acetoxybenzaldehyde, 4-pivaloyloxybenzaldehyde, 4-propanoyloxybenzaldehyde, 4-ethoxycarbonyloxybenzaldehyde, 4-benzyloxylcarbonyloxybenzaldehyde, 4-silyloxybenzaldehyde, and the like can be mentioned. Further, as preferable compounds of those shown in formula (2), for example trimethylcinamylsilane, tin tributylcinnamyl, boron dimethylcinnamyl and the like can be mentioned. As the compounds shown in formula (3), for example methoxybenzene, ethoxybenzene, and benzyloxybenzene and the like are preferable.

In this reaction step, for example, an acid catalyst such as a Lewis acid such as HfCl⁴ or a protonic acid or the like, and as a cocatalyst, trimethylsilyl trifluoromethanesulfonate (TMSOTf) or the like are used. As the cocatalyst, in addition to the above TMSOTf, trimethylsilyl chloride or the like can be used, and as a Lewis acid, in addition to the above, group IV metal salts such as $Hf(OTf)_4$, $TiCl_4$, $TiCl_2(OTf)_2$ and the like, group III metal salts such as $AlCl_3$, $BCl_3$, $Sc(OTf)_3$ and the like, and group II metal salts such as $SnCl_2$, $Sn(OTf)_2$ and the like can be used. Further, as a protonic acid, hydrochloric acid, sulfuric acid, nitric acid, hydrobromic acid, trifluoroacetic acid, trifluoromethanesulfonic acid and the like can be used. These may be used alone, or two or more may be used together. Further, the reaction temperature is from 0 to 40° C., and may be room temperature. The reaction time is from 1 to 10 hours.

Step 2 (Cyclization Reaction Step)

Next, the isomeric mixture obtained in the above step is subjected to a halogen induced carbon cyclization reaction in the presence of a solvent such as diethyl ether, methylene chloride or the like, using a halogenating agent such as N-chlorosuccinic acid imide, N-bromosuccinic acid imide, N-iodosuccinic acid imide, $I(Py)_2BF_4$ and the like, and an acid such as $HBF_4$, $BF_3.OEt_2$, $CF_3SO_3H$ and the like, to obtain an isomeric mixture of the compound shown by formula (5).

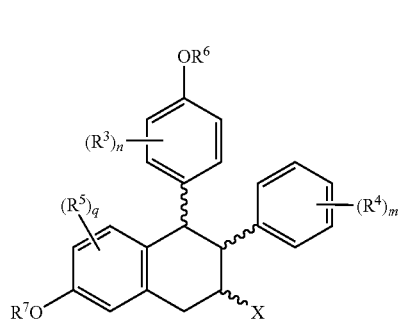

(5)

(in the formula, $R^3$ to $R^7$ and n, m, and q are respectively the same as above, and further, X is a halogen atom and the wavy line is a bond of an R configuration or S configuration).

This reaction is carried out from −78° C. to room temperature.

This isomeric mixture is a mixture of the compounds shown by formula (5), but specifically is a mixture of a total of 8 types of compounds including the respective enantiomers of the compounds shown in formulae (21) to (24) below.

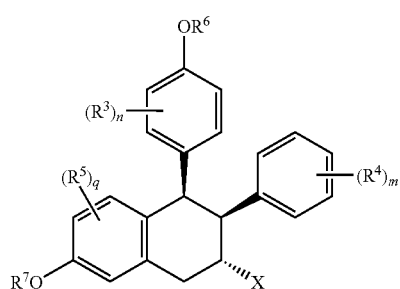

(21)

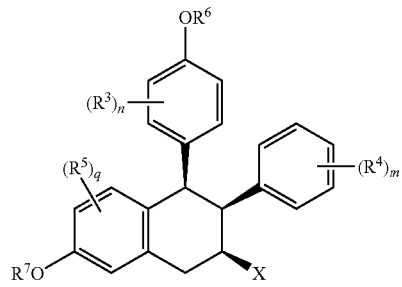

(22)

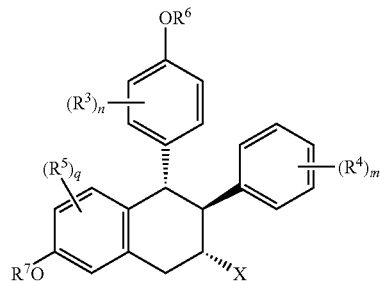

(23)

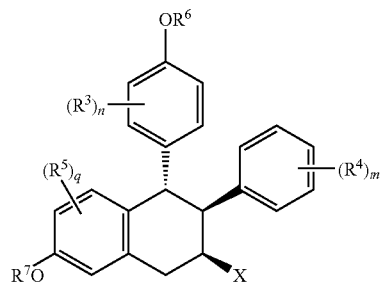

(24)

(in formulae (21) to (24), $R^3$ to $R^7$, X, n, m, and q are the same as above).

Step 3 (Elimination Step of Acyl Group and Iodine)

The isomeric mixture obtained in the above step, with or without separation of the respective compounds, can be subjected to reactions to eliminate a hydrogen halide, rearrange a double bond, and eliminate the $R^1$ group, using a t-butylate, methylate, ethylate or the like, or by using said alcoholate and an amine base such as DBU, DBN, DABCO and the like, to obtain the compound of formula (7). These reactions may be carried out sequentially or simultaneously.

During these reactions, in the case of using an amine base such as DBU or the like, an intermediate including the compound shown by the below formula (25) is generated, but it is not necessary to eliminate this intermediate in the present step, and the above plurality of reaction steps can be allowed to proceed in one reaction vessel. The reaction temperature is from 0° C. to 80° C., and preferably from room temperature to 50° C.

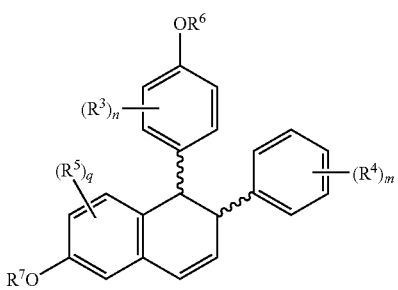

(25)

(in the formula, R³ to R⁷, n, m, and q, and the wavy line are the same as above).

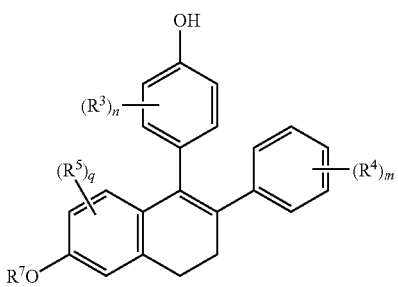

(7)

(in the formula, R³ to R⁷, n, m, and q, and the wavy line are the same as above).

Step 4 (Production Step of Key Intermediate)

The compound of the above formula (7) is subjected to reaction at a reaction temperature from −78° C. to room temperature, in a solvent such as dichloromethane, chloroform, 1,2-dichloroethane or the like, in the presence of a Lewis acid such as boron tribromide ($BBr_3$), $AlBr_3$, TMS or the like or a nucleophile such as thiol or the like, to eliminate the $R^7$ group of the $R^7O$— group at the 7 position of the dihydronaphthalene ring, to obtain the compound of formula (8).

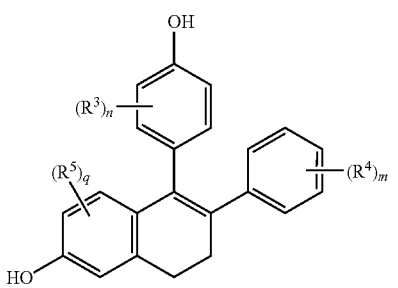

(8)

Step 5 (Side Chain Introduction Step)

The compound of the formula (8) obtained by the above step, in a solvent of dimethylformamide (DMF), dimethylsulfoxide (DMSO) or the like, is subjected to reaction at a reaction temperature of 0° C. to 80° C. with the compound of the below formula (9) in the presence of a basic compound such as sodium hydroxide or the like, and the dihydronaphthalene compound of the present invention shown by the formula (I) is obtained. The obtained compound is a compound where the two hydroxyl groups of the above key intermediate compound have been substituted with the same substituted or unsubstituted aminoalkyl groups.

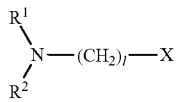

(9)

(in the formula, $R^1$ and $R^2$ are the same as above, X is a halogen, and l is an integer of 2 to 5).

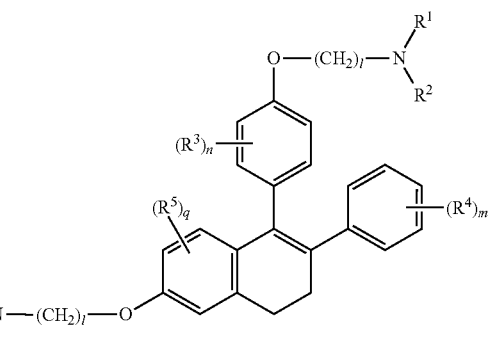

(I)

(in the formula, the definitions of the substituent groups and the like are as previously stated).

Among the compounds of the present invention shown by the formula (I), at least the compounds shown by the formulae (II), (III), and (V) to (VII) show a proteasome inhibition action, and among the compounds of the present invention shown by the formula (I), at least the compounds shown by the formulae (II) and (IV) to (VIII) show an anticancer action. The present invention is the first time a dihydronaphthalene compound such as that of the present invention is recognized to have a proteasome inhibition action or anticancer action, and considering the ease and efficiency of the above synthesis, the technical significance of the present invention is very great.

EXAMPLES

Examples of the present invention are shown below, but the present invention is not limited to these examples.

Example 1

(1) Assembly of Triarylbutene Skeleton by Three Component Concatenation Reaction 1-(4-methoxyphenyl)-2-phenyl-1-(4-pivaloyloxyphenyl)-3-butene (4)

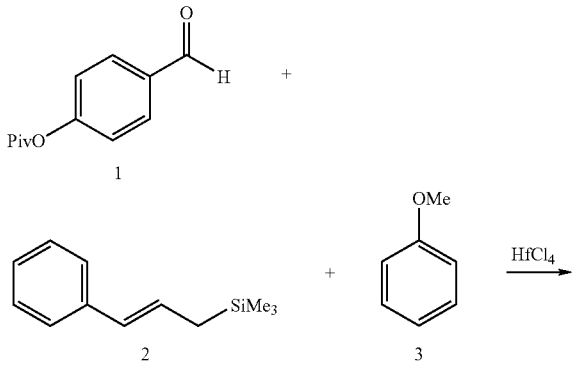

-continued

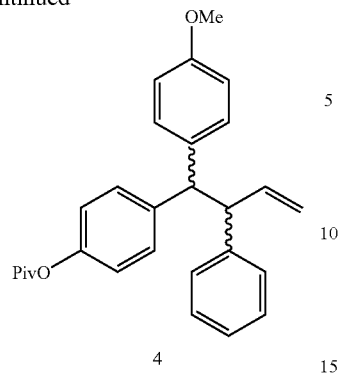

Piv = (CH₃)₃CCO—

-continued

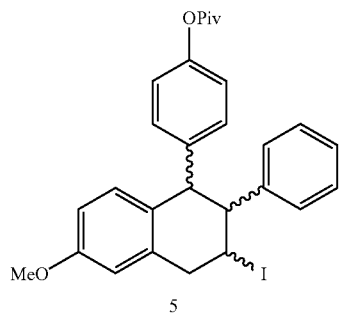

Under an argon atmosphere, hafnium chloride (39.2 mg, 0.122 mmol) is suspended in anisole (3, 0.02 mL), and under ice cooling, an anisole (0.22 mL) solution of 4-(pivaloyloxy) benzaldehyde (1, 25 mg, 0.121 mmol) and trimethylcinnamylsilane (2, 46.7 mg, 0.245 mmol) was slowly added dropwise. After stirring overnight at room temperature, saturated sodium bicarbonate water (5 mL) was poured into the reaction mixture with vigorous stirring, diethyl ether (10 mL) was added and extraction was performed. Extractions were further carried out two times with diethyl ether (10 mL), the organic layers were combined, washed with a saturated sodium chloride aqueous solution (5 mL), dried with anhydrous magnesium sulfate, and concentrated. The residue was purified by thin layer chromatography (hexane:methylene chloride:diethyl ether=4:1:1), and the subject compound (4, 37.7 mg) was obtained as a colorless oily substance (yield 75%, syn/anti mixture).

$^1$H NMR (CDCl₃, tetramethylsilane) δ (ppm): 1.20 and 1.26 (s, 9H), 3.59 and 3.70 (s, 3H), 4.01 (dd, 1H, J=7.8, 11.3 Hz), 4.19 (d, 1H, 11.3 Hz), 4.7-4.9 (m, 2H), 5.8-5.9 (m, 1H), 6.6-7.3 (m, 13H).

Infrared Absorption Spectrum (liquid film method) cm$^{-1}$: 2974, 1749, 1610, 1511, 1462, 1252, 1203, 1167, 1120, 1032, 753, 700.

Mass Spectrum m/e: calculated for $(C_{28}H_{30}O_3+H)^+$= 415.23; found 415.23.

(2) Assembly of Tetrahydronaphthalene Skeleton by Cyclization Reaction 2-iodo-7-methoxy-3-phenyl-4-(4-pivaloyloxyphenyl)-1,2,3,4-tetrahydronaphthalene (5)

Bis(pyridine)iodonium tetrafluoroborate (65.8 mg, 0.177 mmol) was suspended in methylene chloride (3.4 mL), and cooled in a dry ice-acetone bath to −78° C. To this, a methylene chloride (1.8 mL) solution of 1-(4-methoxyphenyl)-2-phenyl-1-(4-pivaloyloxyphenyl)-3-butene (4, 56.0 mg, 0.135 mmol) was added, and further, boron tribromide diethyl ether complex (0.015 mL, 0.118 mmol) was added divided into 3 portions. After this, and after stirring for 1 hr at −78° C., the reaction was stopped by adding a saturated ammonium chloride solution (5 mL), and after returning to room temperature, extraction was performed three times with diethyl ether (10 mL). The organic layers were combined and washed with a saturated sodium chloride solution (10 mL), dried with anhydrous sodium sulfate, and concentrated. The residue was purified with thin layer chromatography (toluene), and the subject compound (5, 51.6 mg) was obtained as a slightly yellow oily substance (yield 71%).

$^1$H NMR (CDCl₃, tetramethylsilane) δ (ppm): 1.32, 1.35 and 1.32 (s, 9H), 3.3 (m, 1H), 3.7-3.9 (m, 5H), 4.2 (d, 1H, J=10.6 Hz), 4.7-4.8 (m, 1H), 6.6-7.2 (m, 12H).

Infrared Absorption Spectrum (liquid film method) cm$^{-1}$: 2972, 1751, 1610, 1510, 1503, 1122, 1031.

Mass Spectrum m/e: calculated for $(C_{28}H_{29}IO_3+H)^+$= 541.12; found 541.12.

(3) Assembly of Dihydronaphthalene Skeleton by Halogen Hydride Elimination Reaction 7-methoxy-3-phenyl-4-(4-pivaloyloxyphenyl)-3,4-dihydronaphthalene (6)

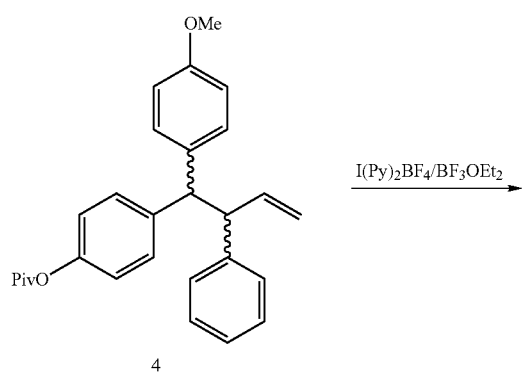

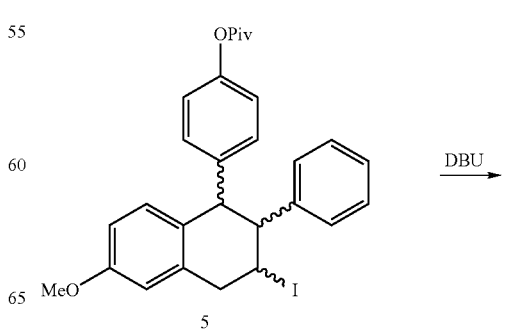

-continued

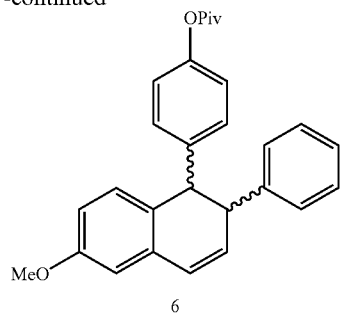

DBU = 1,8-Diazabicyclo[5.4.0]undec-7-ene 2-iodo-7-methoxy-3-phenyl-4-(4-pivaloyloxyphenyl)-1,2,3,4-tetrahydronaphthalene (5, 39.4 mg, 0.0729 mmol) was dissolved in toluene (1.5 mL), and 1,8-diaza-bicyclo[5.4.0]undecene-7 (DBU, 0.035 mL, 0.234 mmol) was added, with heating and stirring at 80° c. for 15 min. After standing to cool, a saturated ammonium chloride aqueous solution (10 mL) was added under ice cooling, vigorously stirred, and next, extraction was carried out adding diethyl ether (10 mL). Extractions were further carried out two times with diethyl ether (10 mL), the organic phases were combined, washed with a saturated sodium chloride aqueous solution, dried with anhydrous sodium sulfate, and concentrated. The residue was purified by thin layer chromatography (benzene:hexane=10:1), and the subject compound (6, 22.7 mg) was obtained as a colorless oily substance (yield=75%).

$^1$H NMR (CDCl$_3$, tetramethylsilane) δ (ppm): 1.34 and 1.36 (s, 9H), 3.76 and 3.80 (s, 3H), 3.84 (dd, 1H, J=4.2, 7.5 Hz), 4.17 (d, 1H, J=7.5 Hz), 5.98 (dd, 1H, 4.2, 9.6 Hz), 6.6-7.2 (m, 12H).

(4) Double Bond Rearrangement Reaction 4-(4-hydroxyphenyl)-7-methoxy-3-phenyl-1,2-dihydronaphthalene (7)

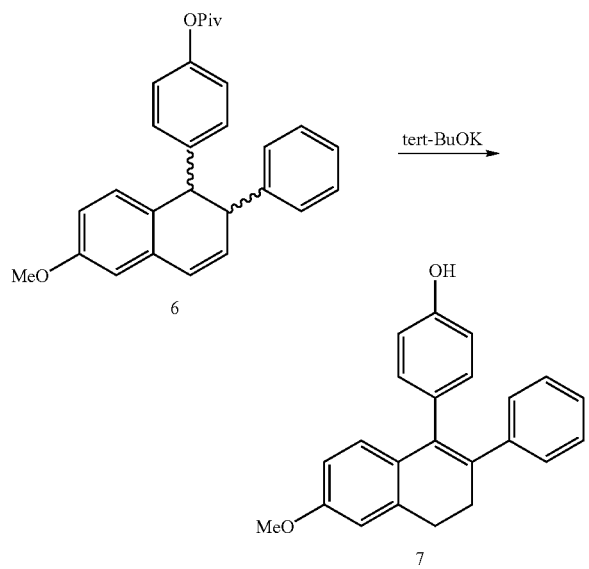

To a dimethyl sulfoxide (0.6 mL) solution of tertiary butoxy potassium (40.3 mg, 0.359 mmol), a dimethyl sulfoxide (0.8 mL) solution of 7-methoxy-3-phenyl-4-(4-pivaloyloxyphenyl)-3,4-dihydronaphthalene (6, 29.3 mg, 0.0710 mmol) was added, and stirred at room temperature for one day and night. After adding saturated ammonium chloride (10 mL) to the reaction mixture with much stirring, extraction was carried out three times with diethyl ether. The organic layers were combined, washed with a saturated sodium chloride solution (10 mL), and after drying with anhydrous sodium sulphate, concentrated. The residue was purified with thin layer chromatography (toluene:ethyl acetate=10:1), to obtain the subject compound (7, 16.0 mg; yield=69%).

$^1$H NMR (CDCl$_3$, tetramethylsilane) δ (ppm): 2.91 (ddd, 2H), 2.75 (ddd, 2H), 3.79 (s, 3H), 6.6-7.2 (m, 12H).

(5) Methyl Elimination Reaction 4-(4-hydroxyphenyl)-7-hydroxy-3-phenyl-1,2-dihydronaphthalene (8)

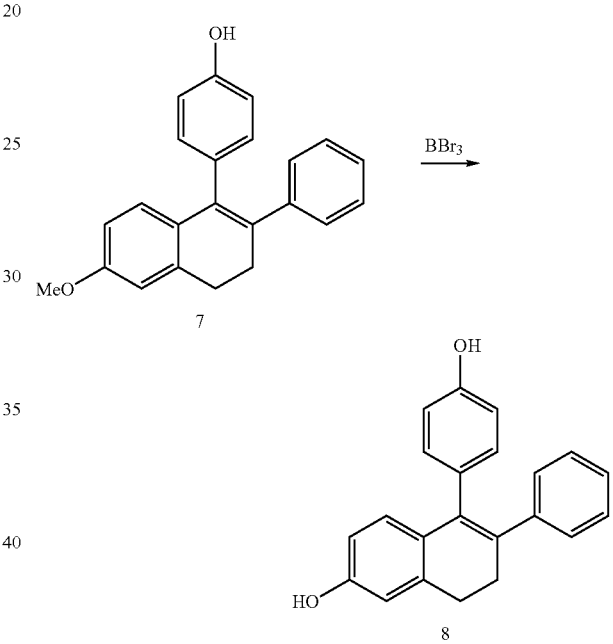

In a reaction vessel, 2.3 ml of dichloromethane was added to the 4-(4-hydroxyphenyl)-7-methoxy-3-phenyl-1,2-dihydronaphthalene (7, 29.7 mg, 0.090 mM) obtained in the above Step (4), and the reaction system was cooled to 0° C. Next, 0.45 ml of a 1 M heptane solution including five equivalents of boron bromide (BBr$_3$) was added. After 1.5 hr had elapsed, thin layer chromatography (n-hexane:ethyl acetate=3:1) was carried out on part of the reaction product, and after confirming that no spot was detected corresponding to the above 4-(4-hydroxyphenyl)-7-methoxy-3-phenyl-1,2-dihydronaphthalene, an aqueous NaHCO$_3$ solution was added and the reaction was stopped. After extracting the reaction product with dichloromethane and ethyl acetate, the organic layer was washed with water and a saturated saline solution, and the organic layer was dried with anhydrous sodium sulfate. After concentrating the organic layer, thin layer chromatography (n-hexane:ethyl acetate 3:1) was carried out, and 27.9 mg of 4-(4-hydroxyphenyl)-7-hydroxy-3-phenyl-1,2-dihydronaphthalene (8) was obtained. The yield was quantitative.

$^1$H NMR (CD$_3$OD) δ (ppm): 7.23-7.07 (m, 5H, Ar), 6.93-6.86 (m, 2H, Ar), 6.79-6.66 (m, 4H, Ar), 6.57 (dd, 1H, J=2.4, 8.4 Hz, Ar), 3.03-2.92 (m, 2H, 1-H), 2.87-2.76 (m, 2H, 2-H).

(6) Side Chain Introduction Reaction (i) 4-[4-(2-pyrrolidine-1-yl-ethoxy)phenyl]-7-(2-pyrrolidine-1-yl-ethoxy)-3-phenyl-1,2-dihydronaphthalene (9)

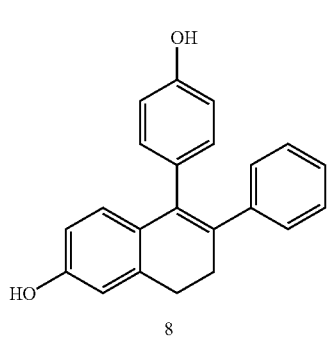
8

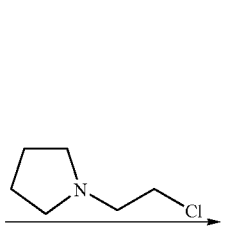

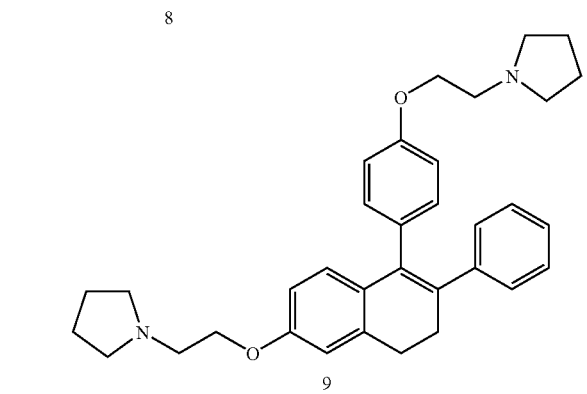
9

To a reaction vessel, 21.6 mg oil containing 60 wt % sodium hydride (6.0 eq NaH) was added, washed with petroleum ether, and dried. Next, 0.9 ml (0.1 M) N,N-dimethylformamide (DMF) was introduced, holding at 0° C. Then 29.0 mg (0.090 mM) of the 4-(4-hydroxyphenyl)-7-hydroxy-3-phenyl-1,2-dihydronaphthalene obtained in the above Step (5) was added to the reaction vessel, and after holding at room temperature for 15 min, it was cooled to 0° C., and 51.0 mg (3.3 eq) of 1-(2-chloroethyl)-pyrrolidine hydrochloride was added, and after reacting at 50° C. for 4 hr, the reaction system was cooled to 0° C. and an ammonium chloride solution was added, and the reaction was stopped. The reaction product was extracted with dichloromethane, and the organic layer was washed with water and a saturated saline solution, and the organic layer was dried with anhydrous sodium sulfate. After concentrating the organic layer, thin layer chromatography (chloroform:methanol:ammonia water=80:1:1) was carried out, and by purifying by further carrying out thin layer chromatography (chloroform:methanol=9:1), 25.2 mg of 4-[4-(2-pyrrolidine-1-yl-ethoxy)phenyl]-7-(2-pyrrolidine-1-yl-ethoxy)-3-phenyl-1,2-dihydronaphthalene ((9), below occasionally referred to as naforidaifen B) was obtained. The yield was 55%.

$^1$H NMR (CDCl$_3$) δ (ppm): 7.14-6.90 (m, 7H, Ar), 6.82-6.68 (m, 4H, Ar), 6.60 (dd, 1H, J=3.0 Hz, 8.7 Hz, Ar), 4.13 (t, 2H, J=6.0 Hz, OCH$_2$), 4.09 (t, 2H, J=6.0 Hz, OCH$_2$), 3.01-2.86 (m, 6H, 1-H, NCH$_2$), 2.82-2.58 (m, 10H, 2-H, pyrrolidinyl 2-H), 1.85-1.76 (m, 8H, pyrrolidinyl 3-H).

(ii) 4-[4-(2-morpholine-1-yl-ethoxy)phenyl]-7-(2-morpholine-1-yl-ethoxy)-3-phenyl-1,2-dihydronaphthalene (10)

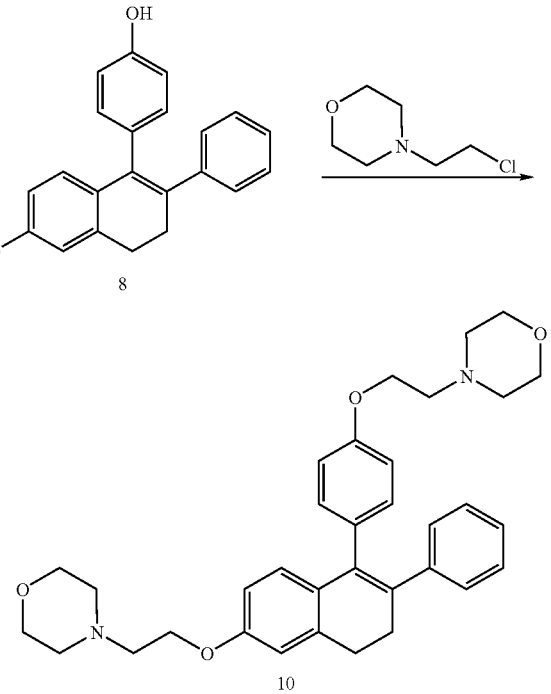

Except for the use of 1-(2-chloroethyl)-morpholine hydrochloride, the same procedure as in the above (i) was carried out, and 94.3 mg of 4-[4-(2-morpholine-1-yl-ethoxy)phenyl]-7-(2-morpholine-1-yl-ethoxy)-3-phenyl-1,2-dihydronaphthalene ((10), below occasionally referred to as naforidaifen D) was obtained. The yield was 79%.

$^1$H NMR (CDCl$_3$) δ (ppm): 7.19-6.93 (m, 7H, Ar), 6.85-6.71 (m, 4H, Ar), 6.61 (dd, 1H, J=2.7, 8.4 Hz, Ar), 4.20-4.06 (m, 4H, OCH$_2$), 3.87-3.67 (m, 8H, morpholinyl 3-H), 3.05-2.73 (m, 8H, 1-H, 2-H, NCH$_2$), 2.71-2.53 (m, 8H, morpholinyl 2-H).

(iii) 4-[4-(2-dimethylamino-1-yl-ethoxy)phenyl]-7-(2-dimethylamino-1-yl-ethoxy)-3-phenyl-1,2-dihydronaphthalene (11)

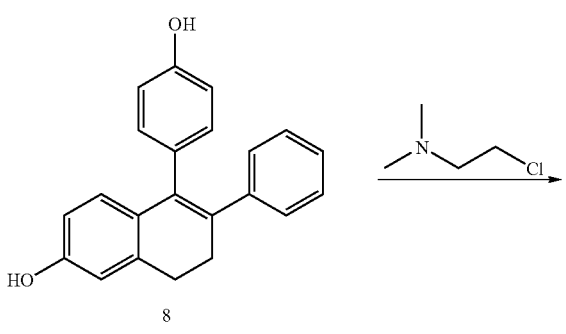

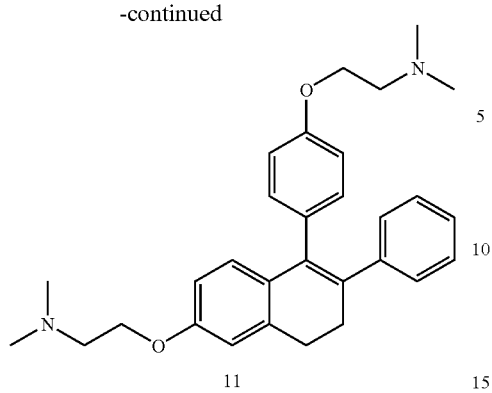

Except for the use of 2-dimethylaminoethyl chloride hydrochloride, the same procedure as in the above (i) was carried out, and 95.9 mg of 4-[4-(2-dimethylamino-1-yl-ethoxy)phenyl]-7-(2-dimethylamino-1-yl-ethoxy)-3-phenyl-1,2-dihydronaphthalene ((11), below occasionally referred to as naforidaifen A) was obtained. The yield was 92%.

$^1$H NMR (CDCl$_3$) δ (ppm): 7.21-6.93 (m, 7H, Ar), 6.80-6.71 (m, 4H, Ar), 6.60 (dd, 1H, J=8.6, 2.6 Hz, Ar), 4.07 (t, 2H, J=5.7 Hz, OCH$_2$), 4.03 (t, 2H, J=5.7 Hz, OCH$_2$), 2.95-2.89 (m, 2H, 1-H), 2.80-2.70 (m, 2H, 2-H), 2.73 (t, 2H, J=5.7 Hz, NCH$_2$), 2.72 (t, 2H, J=5.7 Hz, NCH$_2$), 2.34 (s, 3H×4, NMe).

(iv) 4-[4-(2-piperidine-1-yl-ethoxy)phenyl]-7-(2-piperidine-1-yl-ethoxy)-3-phenyl-1,2-dihydronaphthalene (12)

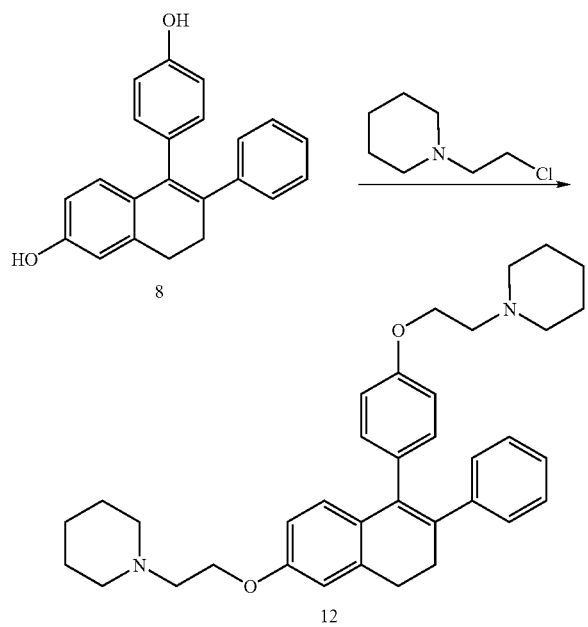

Except for the use of 1-(2-chloroethyl)piperidine hydrochloride, the same procedure as in the above (i) was carried out, and 90.2 mg of 4-[4-(2-piperidine-1-yl-ethoxy)phenyl]-7-(2-piperidine-1-yl-ethoxy)-3-phenyl-1,2-dihydronaphthalene ((12), below occasionally referred to as naforidaifen C) was obtained. The yield was 76%.

$^1$H NMR (CDCl$_3$) δ (ppm): 7.12-6.93 (m, 7H, Ar), 6.78-6.70 (m, 4H, Ar), 6.58 (dd, 1H, J=8.5, 2.4 Hz, Ar), 4.11 (t, 2H, J=6.5 Hz, OCH$_2$), 4.07 (t, 2H, J=5.5 Hz, OCH$_2$), 2.95-2.89 (m, 2H, 1-H), 2.80-2.72 (m, 6H, 2-H, NCH$_2$×2), 2.57-2.42 (m, 2H×4, piperidinyl 2'-H), 1.63-1.59 (m, 2H×4, piperidinyl 3'-H), 1.49-1.39 (m, 2H×2, piperidinyl 4'-H).

(v) 4-[4-(2-diethylamino-1-yl-ethoxy)phenyl]-7-(2-diethylamino-1-yl-ethoxy)-3-phenyl-1,2-dihydronaphthalene (13)

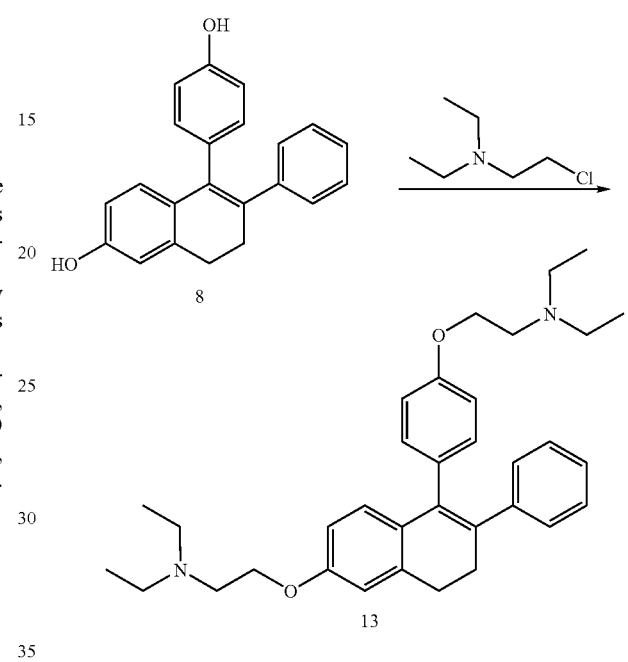

Except for the use of 2-diethylaminoethyl chloride hydrochloride, the same procedure as in the above (i) was carried out, and 40 mg of 4-[4-(2-diethylamino-1-yl-ethoxy)phenyl]-7-(2-diethylamino-1-yl-ethoxy)-3-phenyl-1,2-dihydronaphthalene ((13), below occasionally referred to as naforidaifen E) was obtained. The yield was 41%.

$^1$H NMR (CDCl$_3$) δ (ppm): 7.13-6.93 (m, 7H, Ar), 6.78-6.70 (m, 4H, Ar), 6.58 (dd, 1H, J=8.6, 2.6 Hz, Ar), 4.05 (t, 2H, J=6.3 Hz, OCH$_2$), 4.01 (t, 2H, J=6.3 Hz, OCH$_2$), 2.96-2.84 (m, 6H, 1-H, NCH$_2$×2), 2.79-2.75 (m, 2H, 2-H), 2.64 (q, 2H×4, J=7.0 Hz, NEt), 1.07 (t, 3H×4, J=7.0 Hz, NEt).

(vi) 4-[4-(2-hexahydro-1H-azepin-1-yl-ethoxy)phenyl]-7-(2-hexahydro-1H-azepin-1-yl-ethoxy)-3-phenyl-1,2-dihydronaphthalene (14)

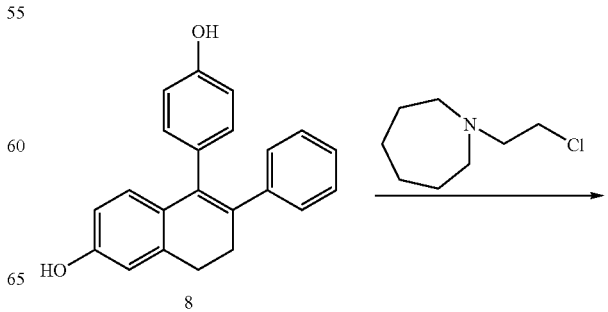

-continued

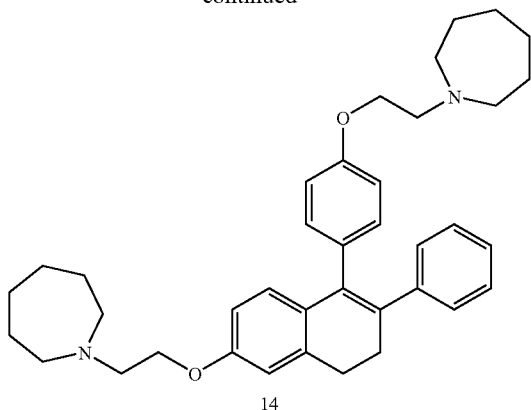

14

Except for the use of N-(2-chloroethyl)-hexahydro-1H-azepin hydrochloride, the same procedure as in the above (i) was carried out, and 46.0 mg of 4-[4-(2-hexahydro-1H-azepin-1-yl-ethoxy)phenyl]-7-(2-hexahydro-1H-azepin-1-yl-ethoxy)-3-phenyl-1,2-dihydronaphthalene ((14), below occasionally referred to as naforidaifen F) was obtained. The yield was 59%.

$^1$H NMR (CDCl$_3$) δ (ppm): 7.10-6.92 (m, 7H, Ar), 6.78-6.70 (m, 4H, Ar), 6.59 (dd, 1H, J=8.6, 2.8 Hz, Ar), 4.07 (t, 2H, J=4.5 Hz, OCH$_2$), 4.03 (t, 2H, J=6.3 Hz, OCH$_2$), 2.97-2.89 (m, 6H, 1-H, NCH$_2$×2), 2.81-2.73 (m, 2H, 2-H, azepinyl 2'-H), 1.79-1.53 (m, 16H, azepinyl 3'-H, 4'-H).

(vii) 4-[4-(3-dimethylamino-1-yl-propoxy)phenyl]-7-(3-dimethylamino-1-yl-propoxy)-3-phenyl-1,2-dihydronaphthalene (15)

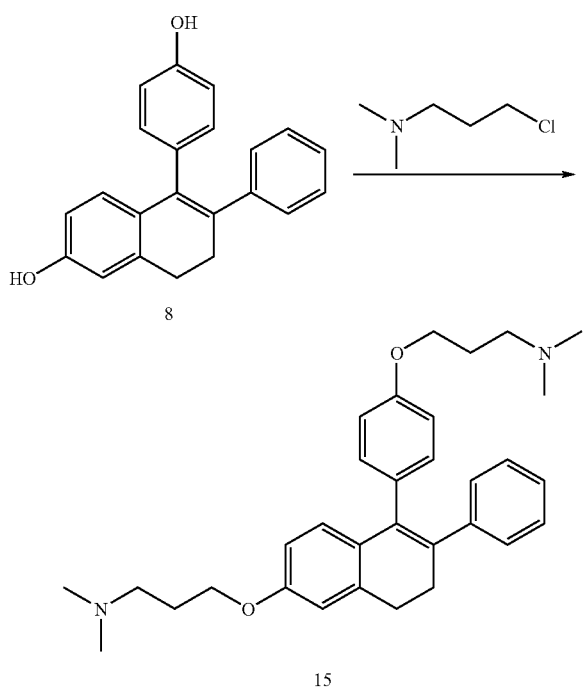

Except for the use of 3-dimethylaminopropyl chloride hydrochloride, the same procedure as in the above (i) was carried out, and 103.9 mg of 4-[4-(3-dimethylamino-1-yl-propoxy)phenyl]-7-(3-dimethylamino-1-yl-propoxy)-3-phenyl-1,2-dihydronaphthalene ((15), below occasionally referred to as naforidaifen G) was obtained. The yield was 86%.

$^1$H NMR (CDCl$_3$) δ (ppm): 7.13-6.92 (m, 7H, Ar), 6.78-6.70 (m, 4H, Ar), 6.58 (dd, 1H, J=8.6, 2.8 Hz, Ar), 4.02 (t, 2H, J=6.3 Hz, OCH$_2$), 3.98 (t, 2H, J=5.7 Hz, OCH$_2$), 2.95-2.90 (m, 2H, 1-H), 2.79-2.72 (m, 2H, 2-H), 2.45 (t, 2H×2, J=7.5 Hz, NCH$_2$), 2.26 (s, 3H×4, NMe), 2.07-1.88 (m, 2H×2, CH$_2$).

Example 2

The experiment below is based on results requested by the present inventors of the Ministry of Education, Culture, Sports, Science and Technology Cancer Specified Research Area Chemotherapy Basic Information Support Group.

The proteasome inhibition activity of 4-[4-(2-pyrrolidine-1-yl-ethoxy)phenyl]-7-(2-pyrrolidine-1-yl-ethoxy)-3-phenyl-1,2-dihydronaphthalene (below referred to as naforidaifen B) was tested as follows.

Chymotrypsin-Like Activity Inhibition Test

1) To 20S proteasome, naforidaifen B adjusted to a concentration of 10 µM was added, and incubated at 30° C. for 10 min.

2) To the above test system, fluorescence labeled chymotrypsin including a 20S proteasome segmenting sequence was added, and reacted for 1 hr at 30° C.

3) The fluorescent substance (AMC) released by the above reaction was excited with 360 nm light and assayed with 460 nm light.

4) A test system to which naforidaifen B was not added was measured in the same way as (1) to (3) above, and the enzyme activity for the case of using naforidaifen B was measured.

5) Stepwise diluted solutions containing naforidaifen B were prepared, and after carrying out the same evaluations as in (1) to (4), the 50% inhibition concentration (IC$_{50}$) was determined.

6) As a positive control of the enzyme activity, the known proteasome inhibitors Clasto-Lactacystin β-Lactone (Lactacystin activator) and MGI32 were evaluated with the steps (1) to (5).

Caspase-Like Activity Inhibition Test

1) To 20S proteasome, naforidaifen B adjusted to a concentration of 10 µM was added, and incubated at 30° C. for 10 min.

2) To the above test system, fluorescence labeled caspase including a 20S proteasome segmenting sequence was added, and reacted for 1 hr at 30° C.

3) The fluorescent substance (AMC) released by the above reaction was excited with 360 nm light and assayed with 460 nm light.

4) A test system to which naforidaifen B was not added was measured in the same way as (1) to (3) above, and the enzyme activity for the case of using naforidaifen B was measured.

5) Stepwise diluted solutions containing naforidaifen B were prepared, and after carrying out the same evaluations as in (1) to (4), the 50% inhibition concentration (IC$_{50}$) was determined.

6) As a positive control of the enzyme activity, the known proteasome inhibitors Clasto-Lactacystin β-Lactone (Lactacystin activator) and MGI32 were evaluated with the steps (1) to (5).

Trypsin-Like Activity Inhibition Test

1) To 20S proteasome, naforidaifen B adjusted to a concentration of 10 µM was added, and incubated at 30° C. for 10 min.

2) To the above test system, fluorescence labeled trypsin including a 20S proteasome segmenting sequence was added, and reacted for 1 hr at 30° C.

3) The fluorescent substance (AMC) released by the above reaction was excited with 360 nm light and assayed with 460 nm light.

4) A test system to which naforidaifen B was not added was measured in the same way as (1) to (3) above, and the enzyme activity for the case of using naforidaifen B was measured.

5) Stepwise diluted solutions containing naforidaifen B were prepared, and after carrying out the same evaluations as in (1) to (4), the 50% inhibition concentration ($IC_{50}$) was determined.

6) As a positive control of the enzyme activity, the known proteasome inhibitors Clasto-Lactacystin β-Lactone (Lactacystin activator) and MGI32 were evaluated with the steps (1) to (5).

Cathepsin-Like Activity Inhibition Test

1) To 20S proteasome, naforidaifen B adjusted to a concentration of 10 µM was added, and incubated at 30° C. for 10 min.

2) To the above test system, fluorescence labeled cathepsin including a 20S proteasome segmenting sequence was added, and reacted for 1 hr at 30° C.

3) The fluorescent substance (AMC) released by the above reaction was excited with 360 nm light and assayed with 460 nm light.

4) A test system to which naforidaifen B was not added was measured in the same way as (1) to (3) above, and the enzyme activity for the case of using naforidaifen B was measured.

5) Stepwise diluted solutions containing naforidaifen B were prepared, and after carrying out the same evaluations as in (1) to (4), the 50% inhibition concentration ($IC_{50}$) was determined.

6) As a positive control of the enzyme activity, the known proteasome inhibitor Clasto-Lactacystin β-Lactone (Lactacystin activator) and MGI32 were evaluated with the steps (1) to (5).

α-Chymotrypsin-Like Activity Inhibition Test

1) To 20S proteasome, naforidaifen B adjusted to a concentration of 10 µM was added, and incubated at 30° C. for 10 min.

2) To the above test system, fluorescence labeled α-chymotrypsin including a 20S proteasome segmenting sequence was added, and reacted for 1 hr at 30° C.

3) The fluorescent substance (AMC) released by the above reaction was excited with 360 nm light and assayed with 460 nm light.

4) A test system to which naforidaifen B was not added was measured in the same way as (1) to (3) above, and the enzyme activity for the case of using naforidaifen B was measured.

5) Stepwise diluted solutions containing naforidaifen B were prepared, and after carrying out the same evaluations as in (1) to (4), the 50% inhibition concentration ($IC_{50}$) was determined.

6) As a positive control of the enzyme activity, the well-known proteasome inhibitor Clasto-Lactacystin β-Lactone (Lactacystin activator) and MGI32 were evaluated with the steps (1) to (5).

The results are shown below.

Criteria
$IC_{50}$<0.1 µM: +++ (very strong activity)
$IC_{50}$=0.1 to 1 µM: ++ (strong activity)
$IC_{50}$=1 to 10 µM: + (relatively strong activity)
$IC_{50}$>10 µM: ± (weak activity, or no activity)

Results
Primary Evaluation

TABLE 1

| Chymotrypsin-like Activity | | | |
|---|---|---|---|
| Sample | Concentration (µM) | % Control | $IC_{50}$ (µM) |
| Naforidaifen B | 10 | 27.1 | 4.6 |
| Clasto-Lactacystin β-Lactone | 10 | 0 | 0.039 |
| MG132 | 10 | 0 | 0.011 |

Secondary Evaluation

TABLE 2

| Caspase-like Activity | | | |
|---|---|---|---|
| Sample | Concentration (µM) | % Control | $IC_{50}$ (µM) |
| Naforidaifen B | 10 | 16.5 | 2.5 |

TABLE 3

| Trypsin-like Activity | | | |
|---|---|---|---|
| Sample | Concentration (µM) | % Control | $IC_{50}$ (µM) |
| Naforidaifen B | 10 | 35.3 | 8.6 |

Cathepsin B inhibition: (none)
α-chymotrypsin inhibition: (none)

Judgement
Chymotrypsin-like activity: ($IC_{50}$=4.6)
Caspase-like activity: ($IC_{50}$=2.5)
Trypsin-like activity: ($IC_{50}$=8.6)
Proteasome selectivity: (present)

The evaluations are positive, naforidaifen B has inhibition activity with respect to 20S proteasome chymotrypsin-like activity, and the same caspase activity, and the same trypsin activity, and in particular, the $IC_{50}$ of the 20S proteasome caspase-like activity shows a relatively strong activity.

Example 3

In the same way as for Example 2, 4-[4-(2-morpholine-1-yl-ethoxy)phenyl]-7-(2-morpholine-1-yl-ethoxy)-3-phenyl-1,2-dihydronaphthalene (below, referred to as naforidaifen D) was measured for its proteasome inhibition activity. The results are shown below.

Criteria
$IC_{50}$<0.1 µM: +++ (very strong activity)
$IC_{50}$=0.1 to 1 µM: ++ (strong activity)
$IC_{50}$=1 to 10 µM: + (relatively strong activity)
$IC_{50}$>10 µM: ± (weak activity, or no activity)

Results
Primary Evaluation

TABLE 4

| Chymotrypsin-like Activity | | | |
|---|---|---|---|
| Sample | Concentration (µM) | % Control | $IC_{50}$ (µM) |
| Naforidaifen D | 10 | 22.1 | 6.8 |
| Clasto-Lactacystin β-Lactone | 10 | 0 | 0.039 |
| MG132 | 10 | 0 | 0.011 |

Secondary Evaluation

TABLE 5

| Caspase-like Activity | | | |
|---|---|---|---|
| Sample | Concentration (μM) | % Control | $IC_{50}$ (μM) |
| Naforidaifen D | 10 | 21.9 | 4.6 |

TABLE 6

| Trypsin-like Activity | | | |
|---|---|---|---|
| Sample | Concentration (μM) | % Control | $IC_{50}$ (μM) |
| Naforidaifen D | 10 | 21.6 | 4.1 |

Cathepsin B inhibition: (none)
α-chymotrypsin inhibition: (none)
Judgement
    Chymotrypsin-like activity: ($IC_{50}$=6.8)
    Caspase-like activity: ($IC_{50}$=4.6)
    Trypsin-like activity: ($IC_{50}$=4.1)
    Proteasome selectivity: (present)
    The evaluations are positive, naforidaifen D has inhibition activity with respect to 20S proteasome chymotrypsin-like activity, and the same caspase activity, and the same trypsin activity, and in particular, the $IC_{50}$ of the 20S proteasome trypsin-like activity shows a relatively strong activity.

Example 4

In the same way as for Example 2, 4-[4-(2-dimethylamino-1-yl-ethoxy)phenyl]-7-(2-dimethylamino-1-yl-ethoxy)-3-phenyl-1,2-dihydronaphthalene (below, referred to as naforidaifen A) was measured for its proteasome inhibition activity. The results are shown below.
Criteria
    $IC_{50}$<0.1 μM: +++ (very strong activity)
    $IC_{50}$=0.1 to 1 μM: ++ (strong activity)
    $IC_{50}$=1 to 10 μM: + (relatively strong activity)
    $IC_{50}$>10 μM: ± (weak activity, or no activity)
Results
Primary Evaluation

TABLE 7

| Chymotrypsin-like Activity | | | |
|---|---|---|---|
| Sample | Concentration (μM) | % Control | $IC_{50}$ (μM) |
| Naforidaifen A | 10 | 99.5 | >10 |
| Clasto-Lactacystin β-Lactone | 10 | 0 | 0.039 |
| MG132 | 10 | 0 | 0.011 |

Judgement
Chymotrypsine-like activity: ($IC_{50}$>10)
The evaluations are negative, the $IC_{50}$ of the 20S proteasome chymotrypsin-like activity of naforidaifen A was >10 μM.

Example 5

In the same way as for Example 2, 4-[4-(2-piperidine-1-yl-ethoxy)phenyl]-7-(2-piperidine-1-yl-ethoxy)-3-phenyl-1,2-dihydronaphthalene (below, referred to as naforidaifen C) was measured for its proteasome inhibition activity. The results are shown below.
Criteria
    $IC_{50}$<0.1 μM: +++ (very strong activity)
    $IC_{50}$=0.1 to 1 μM: ++ (strong activity)
    $IC_{50}$=1 to 10 μM: + (relatively strong activity)
    $IC_{50}$>10 μM: ± (weak activity, or no activity)
Results
Primary Evaluation

TABLE 8

| Chymotrypsin-like Activity | | | |
|---|---|---|---|
| Sample | Concentration (μM) | % Control | $IC_{50}$ (μM) |
| Naforidaifen C | 10 | 25.9 | 3.2 |
| Clasto-Lactacystin β-Lactone | 10 | 0 | 0.039 |
| MG132 | 10 | 0 | 0.011 |

Secondary Evaluation

TABLE 9

| Caspase-like Activity | | | |
|---|---|---|---|
| Sample | Concentration (μM) | % Control | $IC_{50}$ (μM) |
| Naforidaifen C | 10 | 31.3 | 5.1 |

TABLE 10

| Trypsin-like Activity | | | |
|---|---|---|---|
| Sample | Concentration (μM) | % Control | $IC_{50}$ (μM) |
| Naforidaifen C | 10 | 196.2 | >10 |

Cathepsin B inhibition: (none)
α-chymotrypsin inhibition: (none)
Judgement
    Chymotrypsin-like activity: ($IC_{50}$=3.2)
    Caspase-like activity: ($IC_{50}$=5.1)
    Trypsin-like activity: ($IC_{50}$>10)
    Proteasome selectivity: (present)
    The evaluations are positive, naforidaifen C has inhibition activity with respect to 20S proteasome chymotrypsin-like activity, and the same caspase activity, and in particular, the $IC_{50}$ of the 20S proteasome chymotrypsin-like activity shows a relatively strong activity.

Example 6

In the same way as for Example 2, 4-[4-(2-diethylamino-1-yl-ethoxy)phenyl]-7-(2-diethylamino-1-yl-ethoxy)-3-phenyl-1,2-dihydronaphthalene (below, referred to as naforidaifen E) was measured for its proteasome inhibition activity. The results are shown below.
Criteria
    $IC_{50}$<0.1 μM: +++ (very strong activity)
    $IC_{50}$=0.1 to 1 μM: ++ (strong activity)
    $IC_{50}$=1 to 10 μM: + (relatively strong activity)
    $IC_{50}$>10 μM: ± (weak activity, or no activity)

Results
Primary Evaluation

TABLE 11

| Chymotrypsin-like Activity | | | |
|---|---|---|---|
| Sample | Concentration (μM) | % Control | IC$_{50}$ (μM) |
| Naforidaifen E | 10 | 49.6 | 9.9 |
| Clasto-Lactacystin β-Lactone | 10 | 0 | 0.039 |
| MG132 | 10 | 0 | 0.011 |

Secondary Evaluation

TABLE 12

| Caspase-like Activity | | | |
|---|---|---|---|
| Sample | Concentration (μM) | % Control | IC$_{50}$ (μM) |
| Naforidaifen E | 10 | 54.6 | >10 |

TABLE 13

| Trypsin-like Activity | | | |
|---|---|---|---|
| Sample | Concentration (μM) | % Control | IC$_{50}$ (μM) |
| Naforidaifen E | 10 | 162.2 | >10 |

Cathepsin B inhibition: (none)
α-chymotrypsin inhibition: (none)
Judgement
    Chymotrypsin-like activity: (IC$_{50}$=9.9)
    Caspase-like activity: (IC$_{50}$>10)
    Trypsin-like activity: (IC$_{50}$>10)
    Proteasome selectivity: (present)
    The evaluations are positive, naforidaifen E has inhibition activity with respect to 20S proteasome chymotrypsin-like activity.

Example 7

In the same way as for Example 2, 4-[4-(2-hexahydro-1H-azepin-1-yl-ethoxy)phenyl]-7-(2-hexahydro-1H-azepin-1-yl-ethoxy)-3-phenyl-1,2-dihydronaphthalene (below, referred to as naforidaifen F) was measured for its proteasome inhibition activity. The results are shown below.
Criteria
    IC$_{50}$<0.1 μM: +++ (very strong activity)
    IC$_{50}$=0.1 to 1 μM: ++ (strong activity)
    IC$_{50}$=1 to 10 μM: + (relatively strong activity)
    IC$_{50}$>10 μM: ± (weak activity, or no activity)
Results
Primary Evaluation

TABLE 14

| Chymotrypsin-like Activity | | | |
|---|---|---|---|
| Sample | Concentration (μM) | % Control | IC$_{50}$ (μM) |
| Naforidaifen F | 10 | 34.2 | 4.3 |
| Clasto-Lactacystin β-Lactone | 10 | 0 | 0.039 |
| MG132 | 10 | 0 | 0.011 |

Secondary Evaluation

TABLE 15

| Caspase-like Activity | | | |
|---|---|---|---|
| Sample | Concentration (μM) | % Control | IC$_{50}$ (μM) |
| Naforidaifen F | 10 | 39.1 | 5.1 |

TABLE 16

| Trypsin-like Activity | | | |
|---|---|---|---|
| Sample | Concentration (μM) | % Control | IC$_{50}$ (μM) |
| Naforidaifen F | 10 | 250.7 | >10 |

Cathepsin B inhibition: (none)
α-chymotrypsin inhibition: (none)
Judgement
    Chymotrypsin-like activity: (IC$_{50}$=4.3)
    Caspase-like activity: (IC$_{50}$=5.1)
    Trypsin-like activity: (IC$_{50}$>10)
    Proteasome selectivity: (present)
    The evaluations are positive, naforidaifen F has inhibition with respect to 20S proteasome chymotrypsin-like activity, and the same caspase activity, and in particular, the IC$_{50}$ of the 20S proteasome chymotrypsin-like activity shows a relatively strong activity.

Example 8

In the same way as for Example 2, 4-[4-(3-dimethylamino-1-yl-propoxy)phenyl]-7-(3-dimethylamino-1-yl-propoxy)-3-phenyl-1,2-dihydronaphthalene (below, referred to as naforidaifen G) was measured for its proteasome inhibition activity. The results are shown below.
Criteria
    IC$_{50}$<0.1 μM: +++ (very strong activity)
    IC$_{50}$=0.1 to 1 μM: ++ (strong activity)
    IC$_{50}$=1 to 10 μM: + (relatively strong activity)
    IC$_{50}$>10 μM: ± (weak activity, or no activity)
Results
Primary Evaluation

TABLE 17

| Chymotrypsin-like Activity | | | |
|---|---|---|---|
| Sample | Concentration (μM) | % Control | IC$_{50}$ (μM) |
| Naforidaifen G | 10 | 104.8 | >10 |
| Clasto-Lactacystin β-Lactone | 10 | 0 | 0.039 |
| MG132 | 10 | 0 | 0.011 |

Judgement
Chymotrypsin-like activity: (IC$_{50}$>10)
    The evaluations are negative, the IC$_{50}$ of the 20S proteasome chymotrypsin-like activity of naforidaifen G was >10 μM.

Example 9

The anti-propagation activity with respect to central nervous system cancer cells of the naforidaifens A to G synthesized in Example 1 was measured as below.

Examination of Inhibition of Propagation of Central Nervous System Cancer Cells

Six types of central nervous system cancer cells (U251, SF-268, SF-295, SF-539, SNB-75, SNB-78) were plated on 96 well plates, and the next day, sample solutions (5 concentrations, $10^{-4}$, $10^{-5}$, $10^{-6}$, $10^{-7}$, and $10^{-8}$ M) were added, and after two days of cultivation, cell proliferation was measured by colorimetry by sulforhodamin B. As the standard of the cell number immediately before the addition of the test substance, the effective concentration $GI_{50}$ (the concentration at which the cell proliferation is restrained to 50% compared to the negative control) was computed by a computer. As a comparison for the inhibition activity, tamoxifen citrate (TAM) was used. The results are shown below in Table 18. In the Table, the concentration units are μM.

TABLE 18

|  | Central Nervous System Cancer Cell Line | | | | | |
| --- | --- | --- | --- | --- | --- | --- |
|  | U251 | SF-268 | SF-295 | SF-539 | SNB-75 | SNB-78 |
| Naforidaifen A | 1.44544 | 1.94984 | 1.73780 | 1.54882 | 1.47911 | 1.81970 |
| Naforidaifen B | 1.58489 | 2.08930 | 1.90546 | 1.86209 | 1.99526 | 1.90546 |
| Naforidaifen C | 1.47911 | 1.73780 | 1.73780 | 1.47911 | 1.51356 | 1.81970 |
| Naforidaifen D | 15.4882 | 38.9045 | 14.4544 | 15.8489 | 20.4174 | 28.8403 |
| Naforidaifen E | 1.51356 | 1.81970 | 1.81970 | 1.86209 | 1.51356 | 1.62181 |
| Naforidaifen F | 1.47911 | 1.69824 | 1.77828 | 1.65959 | 1.73780 | 1.69824 |
| Naforidaifen G | 1.47911 | 1.58489 | 1.77828 | 1.47911 | 1.62181 | 1.77828 |
| TAM | 7.76247 | 12.0226 | 4.16869 | 3.71535 | 5.01187 | 13.4896 |

As can be understood from Table 18, all of the naforidaifens except for naforidaifen D showed a strong proliferation inhibition activity (cytotoxic activity) with respect to central nervous system cancer cells. In particular, it can be understood that naforidaifen A, C, and G showed a relatively good cytotoxic activity (to an extent of 1.4 to 1.9 μM) in general with respect to a various cells. Naforidaifen F had the second most activity with respect to each of the cell lines U251, SF-295, and SNB-78.

Example 10

In the same way as in Example 9, the proliferation inhibition activity of naforidaifens A to G was measured with respect to five types of colon cancer cells (HCC2998, KM-12, HT-29, HCT-15, and HCT-116). The results are shown in Table 19 below. In the Table, the concentration units are μM.

TABLE 19

|  | Colon cancer Cell Line | | | | |
| --- | --- | --- | --- | --- | --- |
|  | HCC2998 | KM-12 | HT-29 | HCT-15 | HCT-116 |
| Naforidaifen A | 1.47911 | 1.86209 | 0.758578 | 1.65959 | 1.09648 |
| Naforidaifen B | 1.58489 | 1.94984 | 1.445440 | 2.34423 | 1.25893 |
| Naforidaifen C | 1.34896 | 1.81970 | 0.549541 | 1.38038 | 1.17490 |
| Naforidaifen D | 17.7828 | 19.9526 | 12.58930 | 19.0546 | 14.7911 |
| Naforidaifen E | 1.58489 | 1.94984 | 0.812831 | 1.58489 | 1.20226 |
| Naforidaifen F | 1.07152 | 1.5882 | 0.501187 | 1.23027 | 1.23027 |
| Naforidaifen G | 1.28825 | 1.65959 | 0.489779 | 1.28825 | 1.09648 |
| TAM | 2.95121 | 3.54813 | 2.344230 | 5.88844 | 7.24436 |

As can be understood from Table 19, all of the naforidaifens except for naforidaifen D showed a strong proliferation inhibition activity (cytotoxic activity) with respect to colon cancer cells. In particular, naforidaifen F had a generally high activity, and an effective concentration on the order of 0.5 to 1.5 μM with respect to all of the five types of colon cancer cell lines was observed. Further, it can also be understood that naforidaifen A, C, and G showed relatively good cytotoxic activity with respect to the HT-29 cell line and the HCT-116 cell line.

Example 11

In the same way as in Example 9, the proliferation inhibition activity of naforidaifens A to G was measured with respect to five types of ovarian cancer cells (OVCAR-3, OVCAR-4, OVCAR-5, OVCAR-8, AND SK-OV-3). The results are shown in Table 20 below. In the Table, the concentration units are μM.

TABLE 20

|  | Ovarian Cancer Cell Line | | | | |
| --- | --- | --- | --- | --- | --- |
|  | OVCAR-3 | OVCAR-4 | OVCAR-5 | OVCAR-8 | SK-OV-3 |
| Naforidaifen A | 1.62181 | 2.13796 | 1.54882 | 2.88403 | 2.29087 |
| Naforidaifen B | 1.58489 | 1.31826 | 1.62181 | 3.80189 | 3.09030 |
| Naforidaifen C | 1.65959 | 2.08930 | 1.25893 | 2.39883 | 2.04174 |
| Naforidaifen D | 17.3780 | 18.6209 | 6.91831 | 25.7040 | 15.4882 |
| Naforidaifen E | 1.86209 | 2.18776 | 1.58489 | 2.45471 | 1.90546 |
| Naforidaifen F | 1.41254 | 1.77828 | 1.31826 | 1.99526 | 1.90546 |
| Naforidaifen G | 1.51356 | 1.77828 | 1.28825 | 1.86209 | 1.73780 |
| TAM | 4.67735 | 6.02560 | 4.36516 | 11.2202 | 19.9526 |

As can be understood from Table 20, all of the naforidaifens except for naforidaifen D showed a strong proliferation inhibition activity (cytotoxic activity) with respect to ovarian cancer cells. In particular, naforidaifens F and G had a generally high activity, and an effective concentration on the order of 1.2 to 1.9 μM with respect to all of the five types of ovarian cancer cell lines was observed. Further, it can also be understood that naforidaifen B showed the highest cytotoxic activity with respect to the OVCAR-4 cell line, and naforidaifen C showed the highest cytotoxic activity with respect to the OVCAR-5 cell line.

Example 12

In the same way as in Example 9, the proliferation inhibition activity of naforidaifens A to G was measured with respect to six types of stomach cancer cells (St-4, MKN1, MKN7, MKN28, MKN45, MKN74). The results are shown in Table 21 below. In the Table, the concentration units are μM.

TABLE 21

|  | Stomac Cancer Cell Line | | | | | |
| --- | --- | --- | --- | --- | --- | --- |
|  | St-4 | MKN1 | MKN7 | MKN28 | MKN45 | MKN74 |
| Naforidaifen A | 1.47911 | 1.47911 | 1.58489 | 1.81970 | 1.73780 | 1.41254 |
| Naforidaifen B | 1.86209 | 1.47911 | 1.58489 | 2.18776 | 1.65959 | 1.65959 |
| Naforidaifen C | 1.58489 | 1.65959 | 1.54882 | 2.51189 | 2.13796 | 1.20226 |
| Naforidaifen D | 15.4882 | 18.6209 | 19.4984 | 45.7088 | 16.5959 | 19.4984 |
| Naforidaifen E | 1.54882 | 1.41254 | 1.41254 | 1.81970 | 1.65959 | 1.23027 |
| Naforidaifen F | 1.58489 | 1.54882 | 1.23027 | 1.81970 | 1.58489 | 1.17490 |
| Naforidaifen G | 1.47911 | 1.51356 | 1.31826 | 1.62181 | 1.47911 | 1.14815 |
| TAM | 6.3095 | 10.2329 | 5.24807 | 6.30957 | 8.31764 | 3.23594 |

As can be understood from Table 21, all of the naforidaifens except for naforidaifen D showed a strong proliferation inhibition activity (cytotoxic activity) with respect to stomach cancer cells. In particular, naforidaifens F and G had a generally high activity, and an effective concentration on the order of 1.1 to 1.8 μM with respect to all of the six types of stomach cancer cell lines was observed. Further, it can also be understood that naforidaifens A and G showed the highest cytotoxic activity with respect to the St-4 cell line, and naforidaifen E showed the highest cytotoxic activity with respect to the MKN1 cell line.

The invention claimed is:

1. A compound having the following formula (I)

(I)

wherein the two substituents

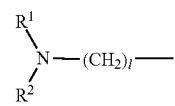

are the same group, $R^1$ and $R^2$ are hydrogen atoms, or are each the same or different alkyl groups, and $R^1$ and $R^2$ may form a monocyclic heterocycle ring together with the nitrogen atom to which they are attached, or further together with one or more of an oxygen atom, sulfur atom, and nitrogen atom; $R^3$, $R^4$ and $R^5$ are each one or more substituent groups selected from the group consisting of a hydrogen atom, alkyl group, acyl group, alicyclic group, aromatic group, halogen atom, acyloxy group, cyano group, and nitro group, where 1 is an integer of 2 to 5, n is an integer of 1 to 4, m is an integer of 1 to 5, and q is an integer of 1 to 3.

2. The compound according to claim 1, having any one of the following formulae (II) to (VII):

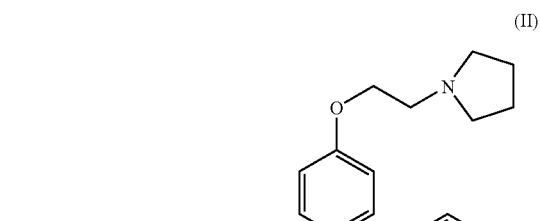

(II)

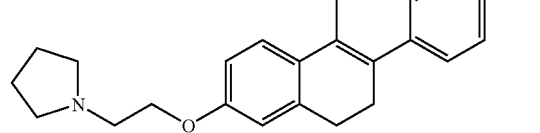

(III)

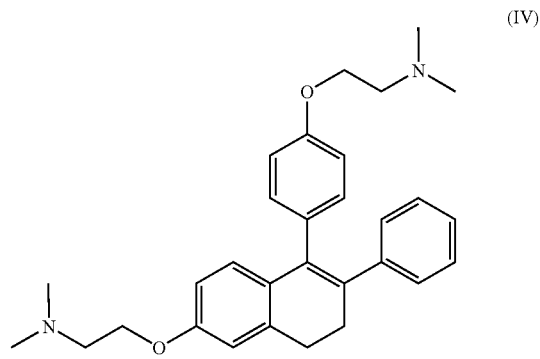

(IV)

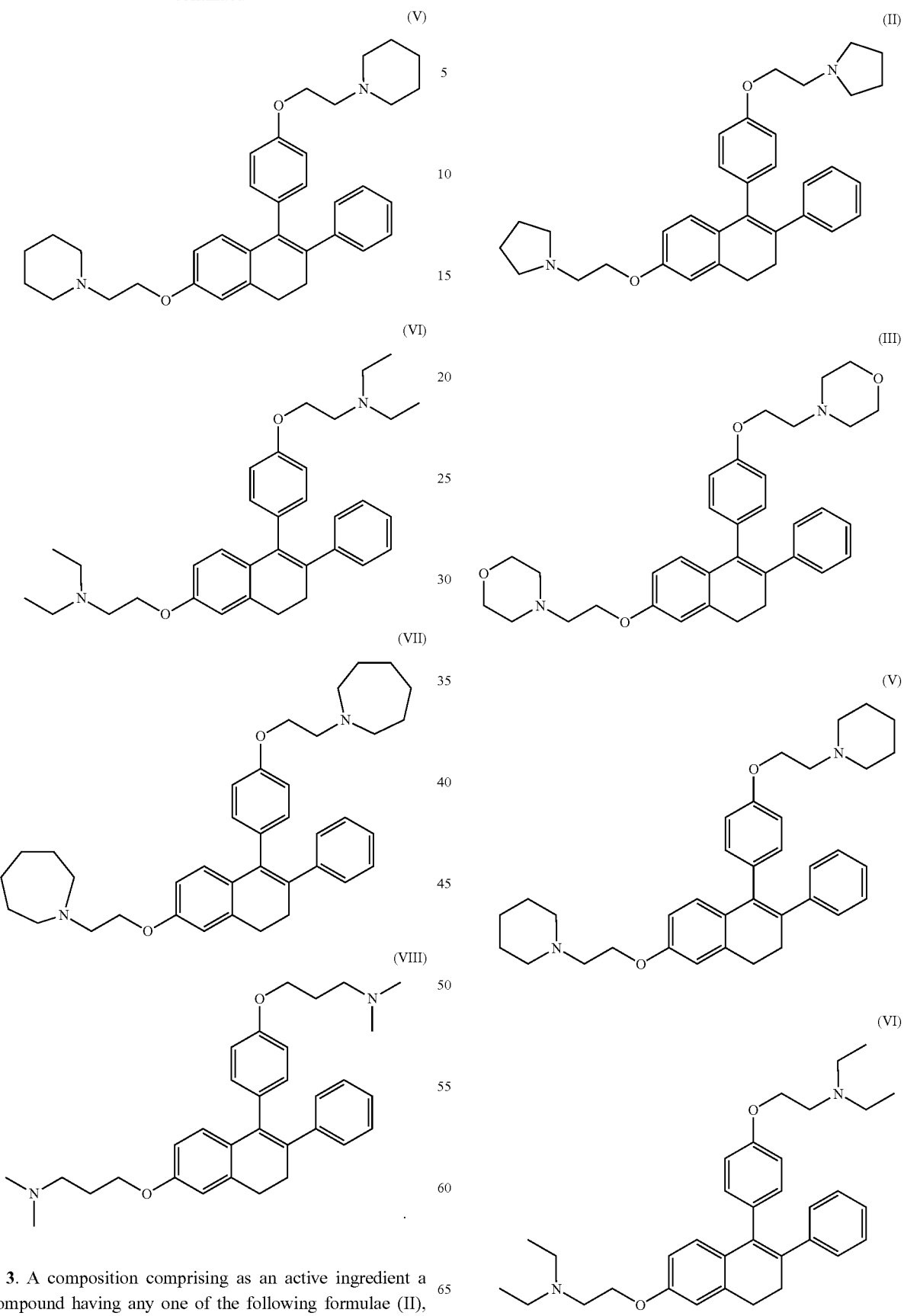
3. A composition comprising as an active ingredient a compound having any one of the following formulae (II), (III), and (V) to (VII)

(VII)
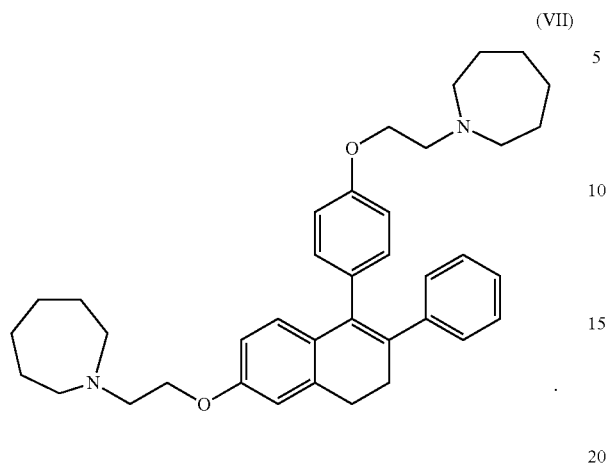
4. A composition comprising as an active ingredient a compound having any one of the following formulae (II), and (IV) to (VIII)
(II)
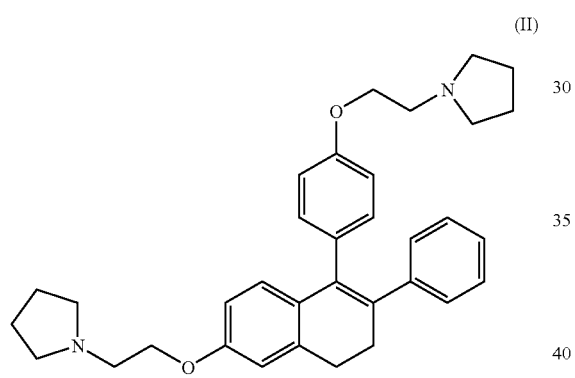
(IV)
(V)
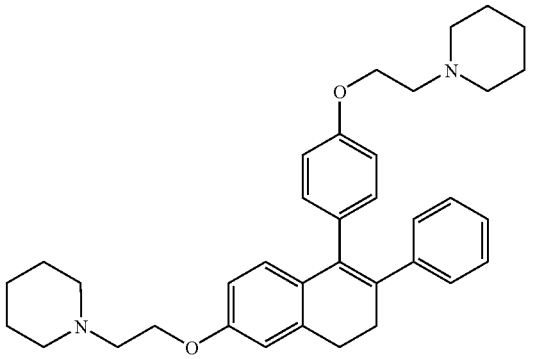
(VI)
(VII)
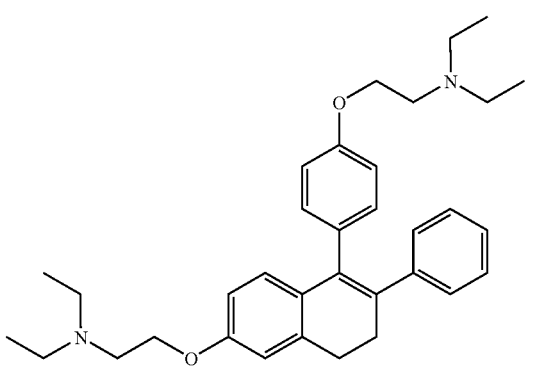
(VIII)
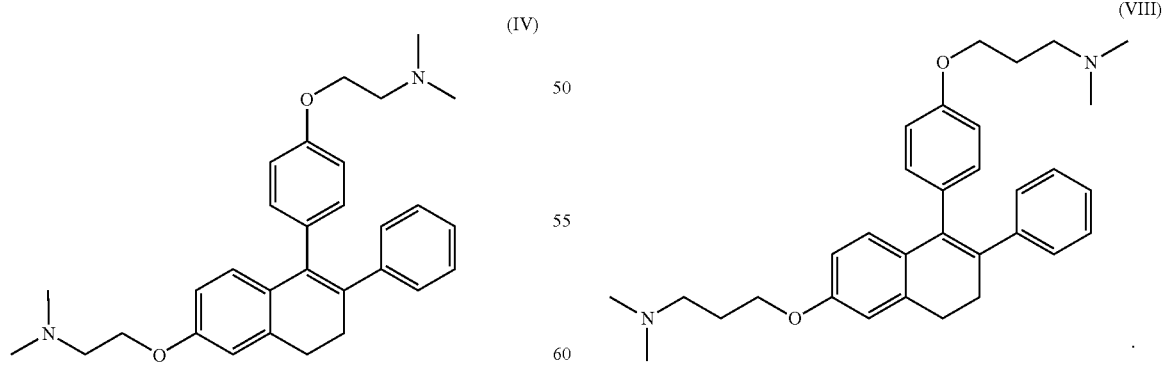
* * * * *